US012751852B1

(12) United States Patent
Luo

(10) Patent No.: US 12,751,852 B1
(45) Date of Patent: Oct. 6, 2026

(54) NASAL DILATION RESPIRATORY DEVICE AND SYSTEM

(71) Applicant: DCSTAR INC, New York, NY (US)

(72) Inventor: David Luo, New York, NY (US)

(73) Assignee: DCSTAR INC, New York, NY (US)

( * ) Notice: Subject to any disclaimer, the term of this patent is extended or adjusted under 35 U.S.C. 154(b) by 0 days.

(21) Appl. No.: 19/315,405

(22) Filed: Aug. 29, 2025

(51) Int. Cl.
*A61F 5/08* (2006.01)

(52) U.S. Cl.
CPC .................................... *A61F 5/08* (2013.01)

(58) Field of Classification Search
CPC . A61F 5/08; A61M 16/0622; A61M 16/0605; A61M 16/0616; A61M 16/0683; A61M 2207/10; A61M 2205/0216
See application file for complete search history.

(56) References Cited

U.S. PATENT DOCUMENTS 11,872,346 B1 * 1/2024 Luo .................. A61M 16/0605
2008/0097517 A1 * 4/2008 Holmes .............. B32B 38/0004
606/199

* cited by examiner

*Primary Examiner* — Vi X Nguyen
(74) *Attorney, Agent, or Firm* — HSML P.C.

(57) ABSTRACT

A nasal dilation respiratory device and system configured to be attached to a user's nasal region to achieve nasal cavity dilation. The device comprises a support member having two end portions, an intermediate portion, and at least one attachment surface, and at least one connector including a first portion and a second portion. The first portion is attached to lateral regions of the user's nose, and the second portion is detachably connected to the attachment surface. The support member applies an outward force to the nasal alar through its end portions to expand the nasal cavity. The connection mechanism may include a hook-and-loop structure, and the support member may be arcuate, arch-shaped, or linear. The device features simple structure, stable wearing, effective dilation, and strong adaptability, suitable for improving nasal airflow and relieving nasal congestion and snoring.

24 Claims, 22 Drawing Sheets

NASAL DILATION RESPIRATORY DEVICE AND SYSTEM

TECHNICAL FIELD

The present disclosure pertains to a nasal dilation respiratory device and system, specifically a respiratory assistance system configured to adhere to a user's nasal region. The system employs a support member and connecting members to achieve nasal dilation and falls within the technical field of medical devices or respiratory assistance technologies. The device is designed to improve the user's respiratory patency and is suitable for the auxiliary treatment of nasal ventilation problems, sleep apnea syndrome (SAS), and other related conditions.

BACKGROUND

With the acceleration of modern life and increasing environmental pressures, public concern for health—particularly respiratory health—has grown significantly. As a critical passage in the human respiratory system, the nasal cavity performs essential functions such as the preliminary filtration, warming, and humidification of inhaled air. The patency of the nasal cavity directly affects respiratory efficiency and overall health status. However, due to various factors such as congenital structural narrowness, soft tissue laxity, allergic rhinitis, and deviated nasal septum, many individuals experience nasal obstruction in daily life. This manifests as difficulty in breathing, sleep apnea, snoring, and even compromised cardiopulmonary function, posing serious risks to life in severe cases.

Current medical research indicates that nasal obstruction not only reduces quality of life but can also lead to chronic fatigue, memory decline, lack of concentration, and other health issues. Particularly during sleep, impaired nasal ventilation can trigger obstructive sleep apnea syndrome (OSAS), the global incidence of which continues to rise and is now widely recognized as a significant health hazard. Accordingly, there is a strong and growing demand across various sectors for auxiliary devices and therapeutic methods aimed at improving nasal airflow.

Presently, auxiliary devices for nasal dilation on the market can generally be classified into two main types: one is an internal dilator, which is placed inside the nasal cavity to support the narrow soft tissue; the other is an external support device, which uses external force to expand the alae and improve nasal ventilation. Although the internal dilator acts directly on the narrow area, it is uncomfortable to wear and has a strong foreign body sensation, which can easily cause local discomfort and infection risks, thereby limiting its widespread application. In contrast, although external support devices have alleviated the problem of nasal obstruction to a certain extent, they generally have defects such as a single fixing method, insufficient wearing stability, limited dilation effect, easy falling off, or skin irritation. In addition, these devices usually lack adaptive designs for different nasal shapes, making it difficult to meet the personalized needs of different users. The design of its fixing structure and expansion force also fails to fully take into account the balance between wearing comfort and effective expansion, resulting in limited user experience and actual efficacy.

In view of the foregoing, existing nasal dilation devices still have significant room for improvement in aspects such as fixation structure, wearing comfort, dilation performance, and adaptability.

SUMMARY

Accordingly, how to design an externally worn nasal cavity dilation device with a reasonable structure, good detachability, and enhanced stability has become a key technical issue in improving user breathing comfort and nasal airflow. Such a device is required to maintain sufficient dilation force while ensuring comfort and stability during wear, minimizing skin irritation and pressure, and accommodating various nasal shapes to provide broader user coverage. Ease of detachment and reusability are also critical factors in enhancing product competitiveness.

In response to the above technical challenges, the present disclosure provides a novel nasal dilation respiratory device and system. By optimizing the structural design and connection mechanism, the device achieves a coordinated balance between dilation force and wearing comfort, improves adaptability and stability, and effectively enhances nasal airflow and user experience, thereby improving the user's quality of life.

The present disclosure addresses the foregoing deficiencies by providing a nasal dilation respiratory device and system that offer structural stability, wearing comfort, and adjustable dilation performance.

The present disclosure provides a nasal dilation respiratory device configured to be attached to a user's nose to dilate a nasal cavity. The device includes:

- a support member, configured to be provided adjacent to a user's nasal region, the support member including two end portions, an intermediate portion, and at least one attachment surface. The two end portions are respectively formed at opposite ends of the support member. The intermediate portion is provided between the two end portions and is configured to correspond to a region between a nasal bridge and a nasal tip of the user during use. The at least one attachment surface is provided on at least one surface of at least one of the two end portions and is configured to connect with at least one connecting member; and
- at least one connecting member that includes a first portion and a second portion. The first portion is configured to be at least partially attached to at least one lateral region of the user's nose. The second portion is configured to be connectable to the at least one attachment surface so as to detachably connect the support member to the at least one connecting member.

In an embodiment, the support member at least partially includes semi-rigid or rigid materials.

In an embodiment, the at least one attachment surface includes at least one structure selected from the group consisting of a hook surface structure, a loop surface structure, and a composite surface structure.

In an embodiment, the intermediate portion of the support member includes at least one structure selected from the group consisting of an arched structure, a curved structure, and a linear structure.

In an embodiment, the first portion of the connecting member includes a medical adhesive material.

In an embodiment, the second portion of the connecting member is configured to be connectable to the at least one attachment surface via hook-and-loop fastening, clasps, magnetic attraction, or chemical adhesive bonding.

The present disclosure further provides a nasal dilation respiratory device configured to be attached to a user's nose to dilate a nasal cavity. The device includes:

- a support member, which is configured to be provided adjacent to a user's nasal region. The support member includes two end portions, an intermediate portion, and at least one attachment surface. The two end portions are respectively formed at opposite ends of the support member. The intermediate portion is provided between the two end portions and is configured to correspond to a region between a nasal bridge and a nasal tip of the user during use. The at least one attachment surface is provided on a surface of at least one of the two end portions and is configured to connect with at least one connecting member; and at least one connecting member that includes a first portion and a second portion. The first portion is configured to be at least partially attached to a lateral region of the user's nose, while the second portion is configured to be detachably adhered to the at least one attachment surface of the support member via hook-and-loop fastening.

In an embodiment, a connection between the at least one attachment surface and the support member is formed by a method selected from the group consisting of integrally molding, ultrasonic welding, adhesive bonding, thermal pressing, and stitching.

In an embodiment, the support member has a symmetrical structure.

In an embodiment, the two end portions of the support member are curved along outer sides of the user's nasal alae to conform to a nasal contour and enhance fixation.

In an embodiment, an outer surface of the first portion of the at least one connecting member is coated with a skin-friendly layer to reduce skin irritation during prolonged wear.

In an embodiment, the hook-and-loop fastening includes a hook surface and a loop surface, with the hook surface and the loop surface configured to cooperate for repeatable attachment.

The present disclosure further provides a nasal dilation respiratory device configured to be attached to a user's nose to dilate a nasal cavity. The device includes:

a support member, which is configured to be provided adjacent to a user's nasal region. The support member includes two end portions, an intermediate portion, and at least one attachment surface. The two end portions are respectively formed at opposite ends of the support member. The intermediate portion is provided between the two end portions and is configured to correspond to a region between a nasal bridge and a nasal tip of the user during use. The at least one attachment surface is at least partially attached to at least one of the two end portions by mechanical connection, chemical bonding, and/or integrally molding;

at least one connecting member that includes a first portion and a second portion. The first portion is configured to be at least partially attached to at least one lateral region of the user's nose, and the second portion is configured to be connected to the at least one attachment surface so as to detachably connect the support member to the at least one connecting member; and the respiratory device has at least one of the following characteristics: the support member has a thickness of at least a portion thereof within a range of 0.1 mm to 20 mm; the support member has a length within a range of 9 mm to 150 mm; the support member has an angle within a range of 30 degrees to 180 degrees; and an area of the at least one connecting member attached to the user's nose is within a range of 0.05 $cm^2$ to 20 $cm^2$.

In an embodiment, the at least one connecting member is configured to be connected to the support member by a method selected from the group consisting of adhesive bonding, hook-and-loop fastening, mechanical engagement, magnetic attraction, and clasp connection, or any combination thereof.

In an embodiment, the support member includes a material having shape memory properties.

In an embodiment, an area of the at least one attachment surface is less than or equal to an area of the second portion.

In an embodiment, the first portion of the connecting member has a shape selected from the group consisting of circular, irregular, and polygonal shapes, which is configured to adapt to different nasal contours and enhance attachment stability.

In an embodiment, different shapes of the first portion correspond to different contact areas, thereby providing directional support and adjustable adhesion force for different regions of the user's nasal alae.

The present disclosure further provides a nasal dilation respiratory system configured to assist a user in dilating a nasal cavity. The system includes:

a support member configured to be provided adjacent to a user's nasal region. The support member includes two end portions and an intermediate portion. The two end portions are respectively formed at opposite ends of the support member and are configured to correspond to outer regions of the user's nasal alae during use. The intermediate portion is provided between the two end portions and is configured to correspond to a region between a nasal bridge and a nasal tip of the user during use;

at least one attachment surface on a surface of at least one of the two end portions and configured to connect with at least one connecting member; and the at least one connecting member, including a first portion and a second portion. The first portion is configured to be at least partially attached to lateral regions of the user's nose, while the second portion is configured to be detachably adhered to the at least one attachment surface via hook-and-loop fastening.

a connection force generated between the support member and the at least one connecting member ranges from 2 gf to 200 gf; and a nasal cavity dilation amplitude generated during use ranges from 0.1 mm to 20 mm.

In an embodiment, the hook-and-loop fastening includes a hook surface and a loop surface, and an adhesive strength between the hook surface and the loop surface is adjustable by varying a fastening area between the hook surface and the loop surface.

In an embodiment, a thickness of the support member at least partially ranges from 0.1 mm to 20 mm.

In an embodiment, the at least one attachment includes a material selected from the group consisting of polyester, polyamide, polyurethane, polyolefin, and composites thereof.

In an embodiment, a metal sheet is embedded within the support member, the metal sheet including a material selected from the group consisting of stainless steel, aluminum alloy, and shape memory alloy.

In an embodiment, the intermediate portion is provided with a serrated structure arranged along a longitudinal direction of the support member to form a plurality of bend angles, thereby providing a compliant structure.

In an embodiment, a contact area between the first portion of the at least one connecting member and the user's nose ranges from 0.05 $cm^2$ to 20 $cm^2$.

The nasal dilation respiratory device and system according to the disclosure described herein provides at least the following beneficial effects:

Traditional nasal dilation products primarily fall into two categories: disposable patch-type dilators and integrated molded-structure dilators. These products generally suffer from issues such as simple structure, weak dilation force, poor adaptability, and high usage cost. On one hand, disposable patch-type dilators mostly rely on skin adhesion for fixation, lacking stable structural support. They generate limited lateral pulling force on the outer nasal alae using only thin films or elastic fibers. Since adhesion is easily affected by factors such as sweat, skin oil, and skin type, these patches tend to shift, peel, or fall off during use, thereby reducing their dilation effectiveness. Moreover, such products are often made from low-cost, single-use patch materials, resulting in limited elasticity and poor structural integrity over time. After several hours of use, patches often undergo fatigue deformation, leading to diminished dilation performance. In addition, most conventional patches are of standard size and lack adjustment mechanisms for different nose shapes. For users with higher nasal bridges or wider nasal alae, fit and comfort are often suboptimal. In contrast, the nasal dilation respiratory device and system of the present disclosure effectively overcome these problems. It employs a combination structure comprising a support member and at least one connecting member. The support member provides stable and directional nasal cavity dilation force with adjustable size and angle, far exceeding the performance of traditional patch-type dilators, thereby enhancing breathing patency. At least one connecting member is partially made of soft, skin-friendly material, with a selectable contact area, which not only enhances wearing comfort, but also ensures a secure connection to the support member via hook-and-loop fastening. This provides strong adaptability and structural stability, making the device resistant to detachment during prolonged wear. Additionally, the support member is reusable, requiring only the replacement of the connecting member, thus reducing long-term usage costs and minimizing material waste, contributing to greater environmental sustainability. As a result, the nasal dilation respiratory device and system offers significant technical advantages over traditional products in terms of dilation effectiveness, comfort, structural stability, adaptability, and cost-efficiency. It is particularly effective in scenarios such as daily relief of breathing obstruction and continuous dilation during physical activity, providing a high-performance alternative to conventional nasal dilation solutions.

In recent years, certain nasal cavity dilation products have attempted to incorporate magnetic attachment structures in an effort to achieve component detachability and structural simplification. While magnetic elements offer some convenience for modular assembly, they present several significant drawbacks in practical applications, particularly in terms of safety, material biocompatibility, cost control, and manufacturing complexity. From a safety perspective, magnets are small, rigid components—especially the miniature magnetic tabs used in at least one connecting member—which are prone to detachment due to friction, impact, or improper handling by the user. In scenarios involving unconscious movement such as sleep or physical activity, accidental inhalation or ingestion of detached magnets may lead to serious medical consequences, including airway obstruction, foreign body ingestion, or gastrointestinal blockage, thereby posing a high safety risk. Such hazards are especially concerning for sensitive populations including infants and elderly individuals. From the standpoint of material composition and biocompatibility, magnets often contain metal alloys such as neodymium-iron-boron (NdFEB). Some users may have sensitivities to metals, and individuals with implanted medical devices such as pacemakers or hearing aids must strictly avoid magnetic interference, further limiting the applicability of such products. By contrast, the present disclosure described herein employs hook-and-loop fastening with no metal components. The structure uses flexible, low-sensitivity materials that minimize skin irritation and are compatible with a broad range of user profiles. Moreover, the magnetic attraction force in such products is not adjustable, which can result in either insufficient adhesion—leading to unintentional detachment—or excessive adhesion—making removal difficult and potentially causing skin pinching or discomfort. In contrast, the bonding strength of the hook-and-loop fastening can be adjusted by varying the contact area and engagement angle, allowing for personalized settings and providing a more flexible and stable structural connection. From a manufacturing and cost-control perspective, magnetic structures require directional alignment, encapsulation, and embedding processes, all of which increase complexity and production costs, while also reducing yield reliability. In contrast, hook-and-loop components are mature, widely available industrial parts that can be directly assembled with at least one connecting member and the support member. They are inexpensive to source, require moderate processing precision, and are well-suited for standardized mass production with higher overall manufacturing efficiency. Therefore, compared to magnet-based connection products, the structure provided by the present disclosure offers significant advantages in terms of safety, adaptability, comfort, cost control, and manufacturing efficiency. It is particularly well-suited for nasal cavity dilation applications that involve continuous daily wear, where a secure, foreign-body-free, and controllable user experience is critical. The device is user- and environmentally friendly, and it helps reduce both the user's usage cost and medical burden.

Among existing nasal cavity dilation products, integrated structural designs are commonly adopted. These products often combine the fixation structure, dilation support component, and contact portion into a single unit in an attempt to simplify both structural configuration and operation. However, such one-piece structures reveal several core issues during actual use. First, there is a functional conflict: the dilation structure possesses sufficient rigidity to provide outward support for nasal cavity dilation, while the contact portion needs a certain degree of softness to ensure wearing comfort. In an integrated design, these two functional regions are inseparable, often resulting in suboptimal dilation performance and user discomfort due to rigid materials causing pressure, friction, or even skin damage to the nasal alae. Second, the integrated structure lacks adjustability, making it difficult to accommodate varying nasal anatomies. In particular, when there are significant individual differences in nasal bridge height or alar width, such monolithic dilators may fail to achieve the appropriate dilation angle or positioning, thereby diminishing the user's overall experience. In contrast, the nasal dilation respiratory device and system of the present disclosure is based on a modular design concept, separating the functions of "dilation force output" and "conformal fixation." Through a structure comprising a support member and at least one connecting member, the device functionally decouples these roles. The support member is made of an adjustable material, and its thickness, length, and bending angle can be customized or adjusted according to the user's needs. The support member delivers a stable outward dilation force through deformation, without affecting the flexible conformability of the at least one connecting member. The at least one connecting member is made of soft, hypoallergenic material with high skin compatibility. Its contact area is adjustable to accommodate different nasal shapes, enhancing wearing comfort. Moreover, the structure employs hook-and-loop fastening, enabling repeatable assembly and disassembly, while also ensuring a strong, stable bond that resists detachment during use. Compared to traditional integrated designs, this modular configuration significantly improves product adaptability, dilation force stability, and overall comfort, enabling a shift from "one-size-fits-all" toward personalized nasal dilation solutions. Additionally, the modular architecture facilitates standardized manufacturing processes and independent quality control for each module, improving production efficiency and product consistency. Therefore, in terms of functional separation, enhanced user experience, individual adaptability, and manufacturing optimization, the present disclosure demonstrates comprehensive superiority over conventional integrated dilation products, representing a substantial optimization and practical evolution in the design philosophy of nasal cavity dilation systems.

DETAILED DESCRIPTION

Figure 1:
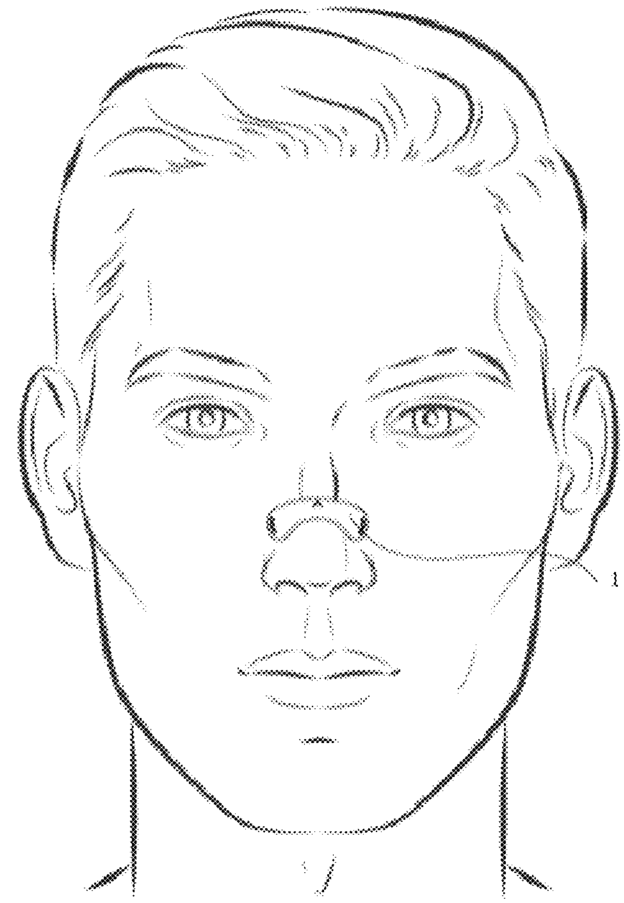
FIG. 1 is a schematic view showing a respiratory device and system being worn according to an embodiment of the present disclosure.
Figure 2:
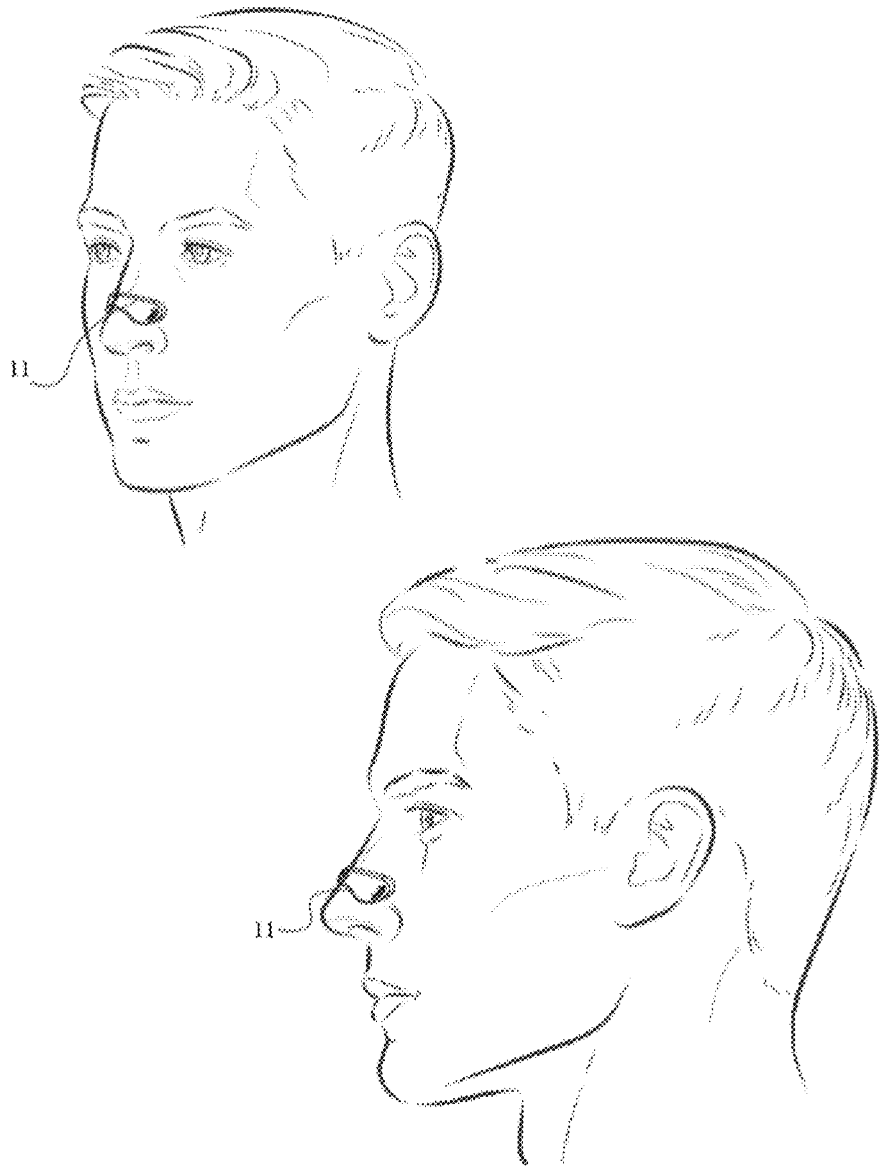
FIG. 2 is another schematic view from a different angle showing the respiratory device and system being worn according to an embodiment of the present disclosure.
Figure 3:
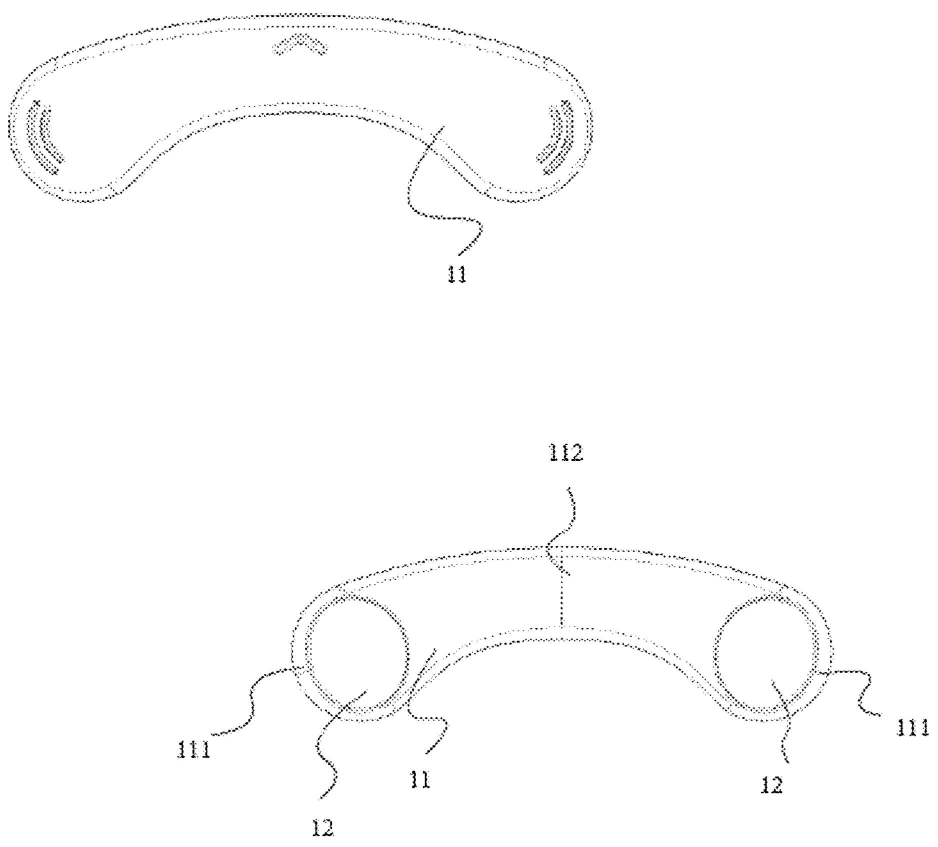
FIG. 3 is a multi-view diagram of the respiratory device and system according to an embodiment of the present disclosure.
Figure 4:
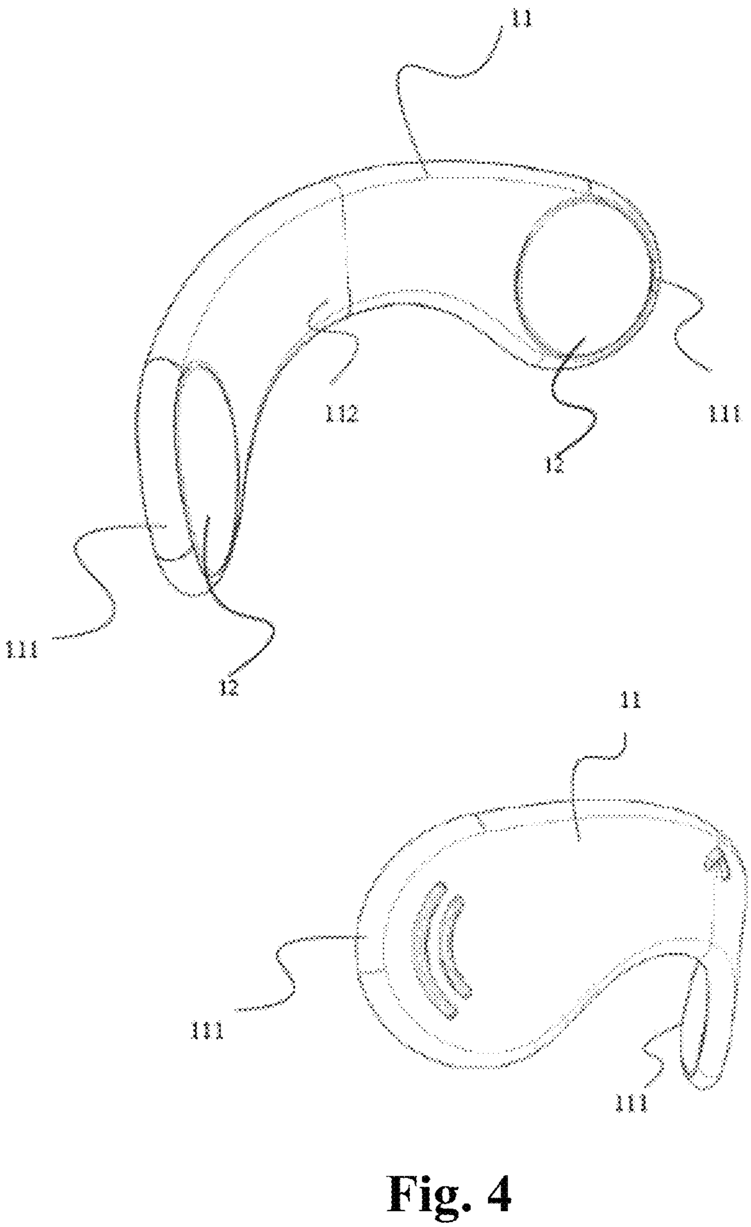
FIG. 4 is a three-dimensional schematic view of the respiratory device and system according to an embodiment of the present disclosure.
Figure 5:
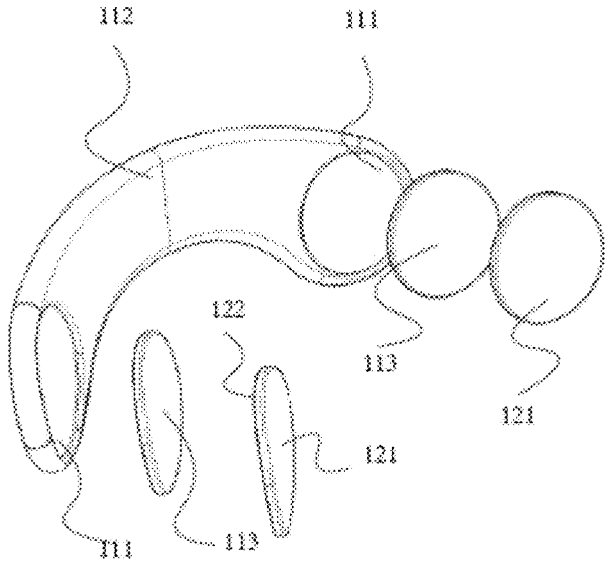
FIG. 5 is an exploded view of the respiratory device and system according to an embodiment of the present disclosure.
Figure 6:
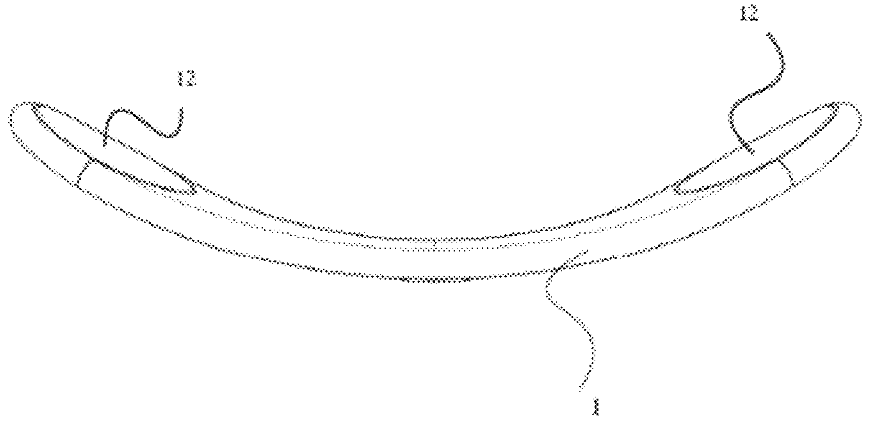
FIG. 6 is a top view of the respiratory device and system according to an embodiment of the present disclosure.
Figure 7:
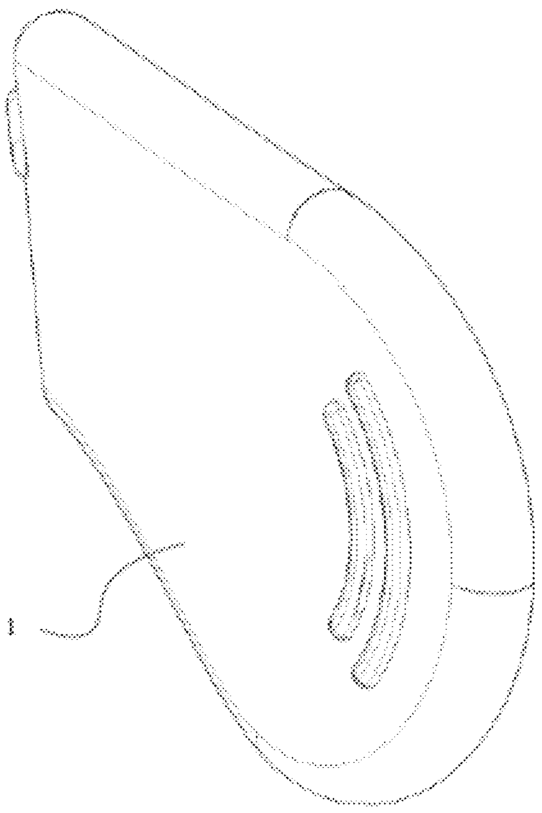
FIG. 7 is a side view of the respiratory device and system according to an embodiment of the present disclosure.

In order to make the above objectives, characteristics, and advantages of the present disclosure more apparent and easier to understand, specific embodiments of the present disclosure are described in detail below with reference to the accompanying drawings. Numerous specific details are set forth in the following description to facilitate a full understanding of the present disclosure. However, it should be understood that the present disclosure may be implemented in ways other than those specifically described herein, and that modifications may be made without departing from the spirit and scope of the present disclosure by those skilled in the art. Therefore, the present disclosure is not limited to the specific embodiments disclosed below.

Compared with existing nasal cavity dilation respiratory system 1, the present disclosure enhances conformity to various facial contours by optimizing the structural form and mechanical parameters of the support member 11. By incorporating multiple types of connecting members 12, it enables reliable and adjustable fixation and dilation of the nasal alae. The support member 11 may be fabricated from various materials to provide effective support while maintaining wearing comfort. It cooperates with the attachment surface 113 provided at the end portions 111 and with different types of connecting members 12 to ensure stability and reliability during use. The system is applicable to a wide range of scenarios, including daily breathing assistance, sleep-related respiratory support, and mild nasal congestion relief. It effectively addresses the shortcomings of existing products with respect to dilation amplitude, structural stability, and fit adaptability.

The following provides a description of several structural examples of the respiratory system 1 of the present disclosure in conjunction with specific embodiments.

Embodiment 1

Referring to FIGS. 1 to 28, the respiratory system 1 of the present embodiment includes: a support member 11 configured to be positioned near the user's nasal region; the support member 11 includes two ends 111, an intermediate portion 112, and at least one attachment surface 113. The two end portions 111 are formed at the opposing ends of the support member 11. The intermediate portion 112 is disposed between the two end portions 111 and is configured to correspond to the region between the user's nasal bridge and nasal tip when worn. At least one attachment surface 113 is disposed on at least one surface of the end portion 111 and is configured to connect with at least one connecting member 12. The at least one connecting member 12 includes a first portion 121 and a second portion 122. The first portion 121 is configured to at least partially attach to the regions on both sides of the user's nose. The second portion 122 is configured to be connected to the attachment surface 113, thereby detachably connecting the support member 11 with the at least one connecting member 12.

Figure 8A:
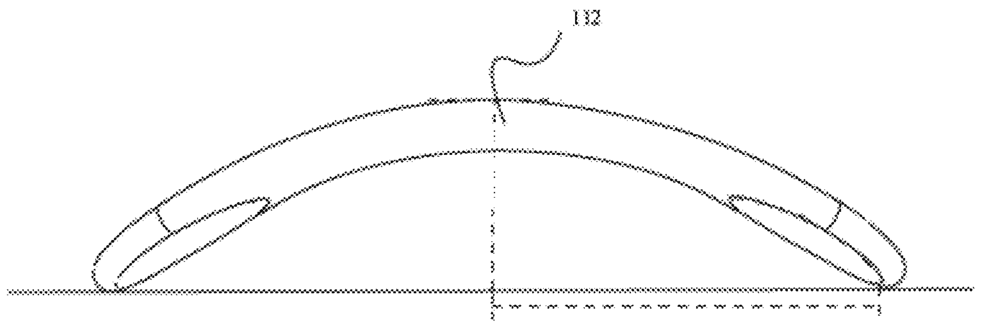
FIG. 8A is a schematic view of an intermediate portion of the respiratory system in an arched shape according to an embodiment of the present disclosure.
Figure 8B:
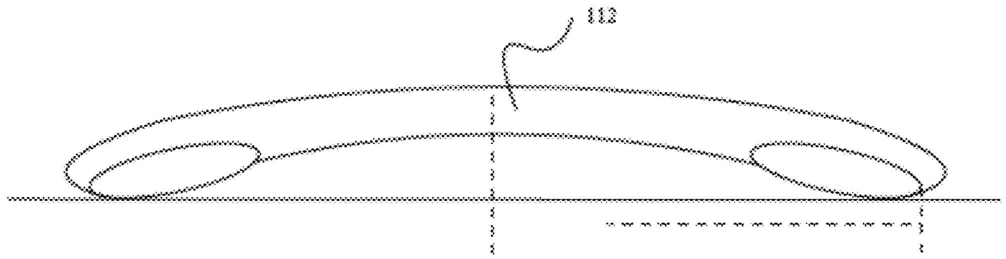
FIG. 8B is a schematic view of an intermediate portion of the respiratory system in an arcuate shape according to an embodiment of the present disclosure.
Figure 8C:
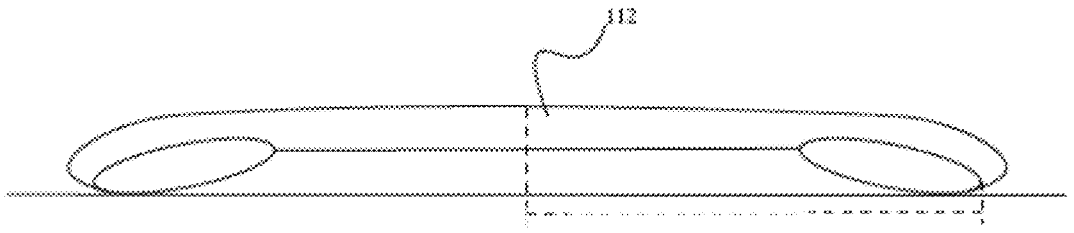
FIG. 8C is a schematic view of an intermediate portion of the respiratory system in a linear shape according to an embodiment of the present disclosure.
Figure 9:
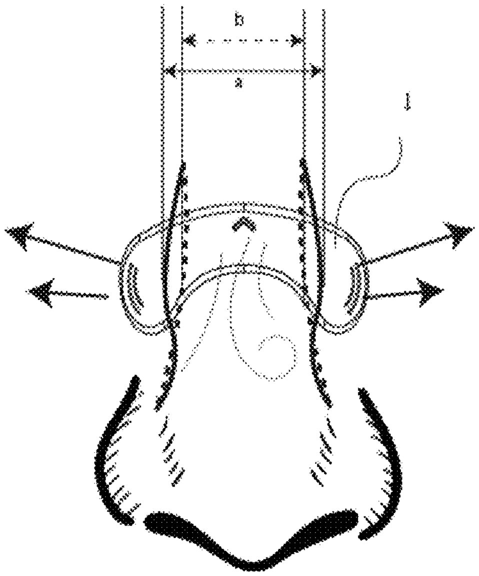
FIG. 9 is a schematic view illustrating dilation force of the respiratory device and system according to an embodiment of the present disclosure.
Figure 10:
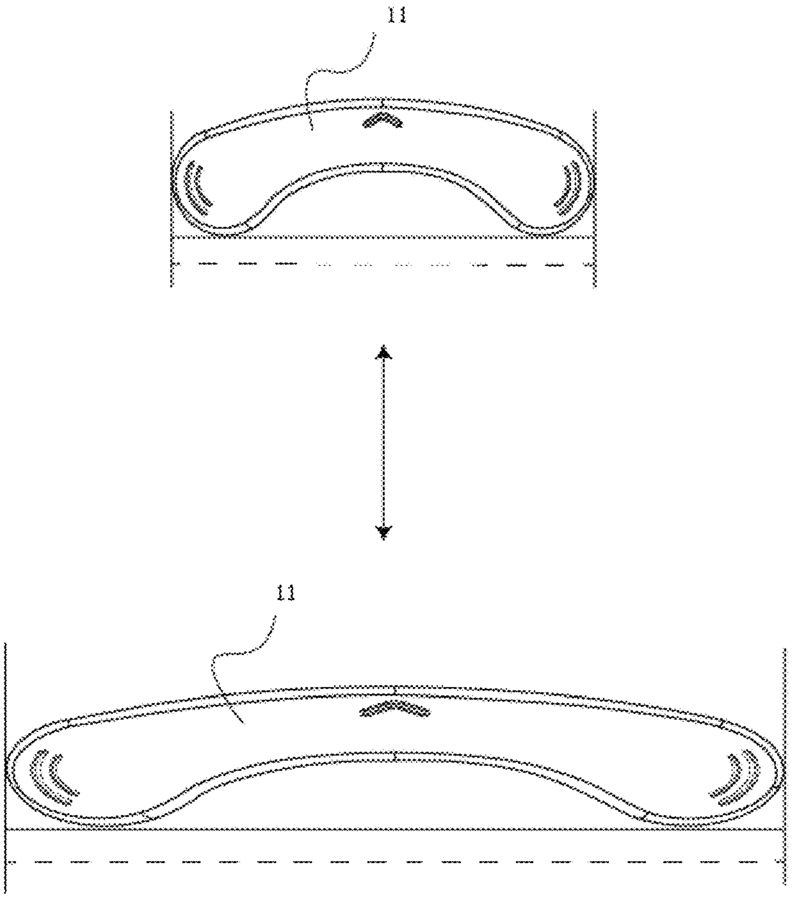
FIG. 10 is a schematic view showing a length range of a support member of the respiratory device and system according to an embodiment of the present disclosure.
Figure 11:
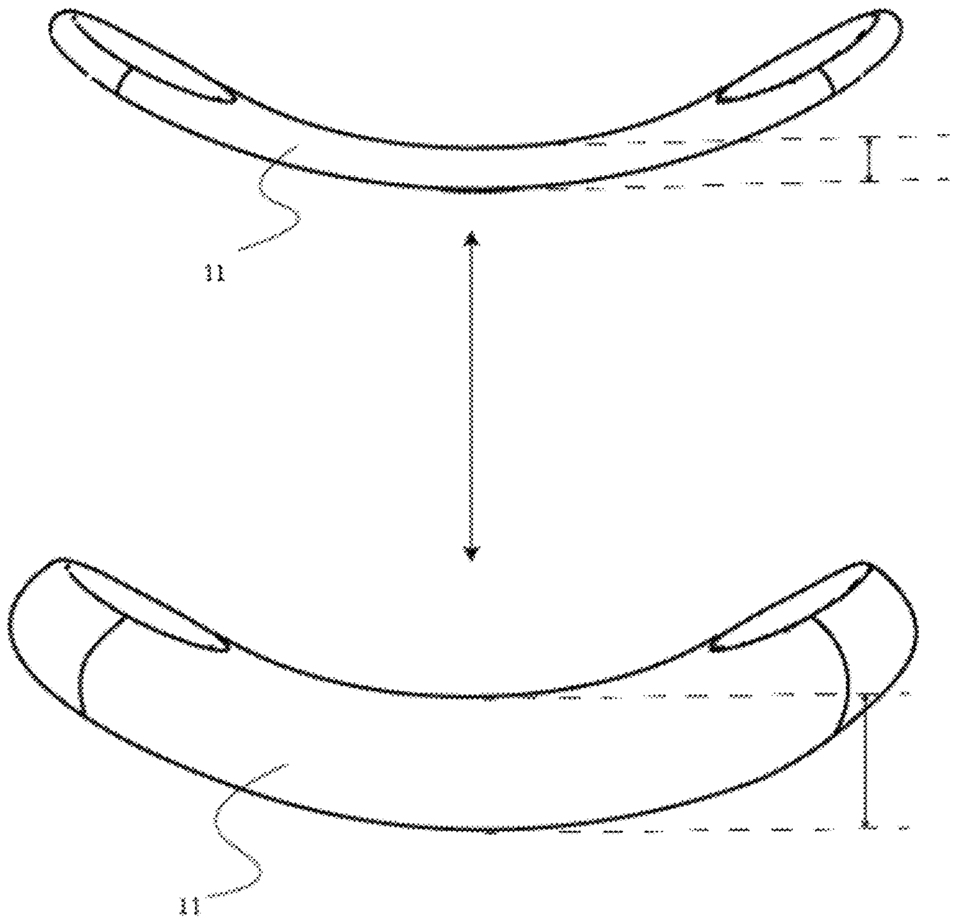
FIG. 11 is a schematic view showing a thickness range of the support member of the respiratory device and system according to an embodiment of the present disclosure.
Figure 12:
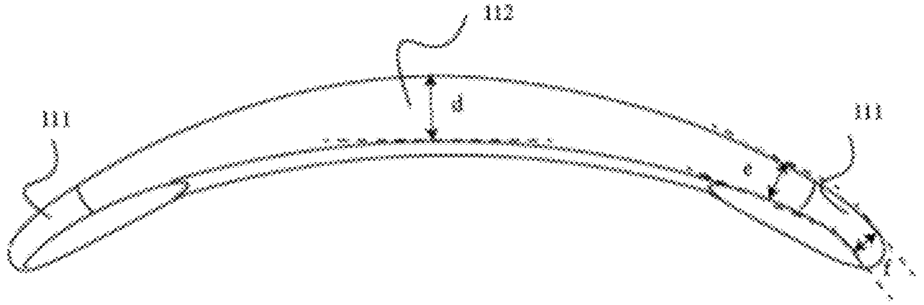
FIG. 12 is a schematic view showing a variation in thickness of the support member of the respiratory device and system according to an embodiment of the present disclosure.
Figure 13:
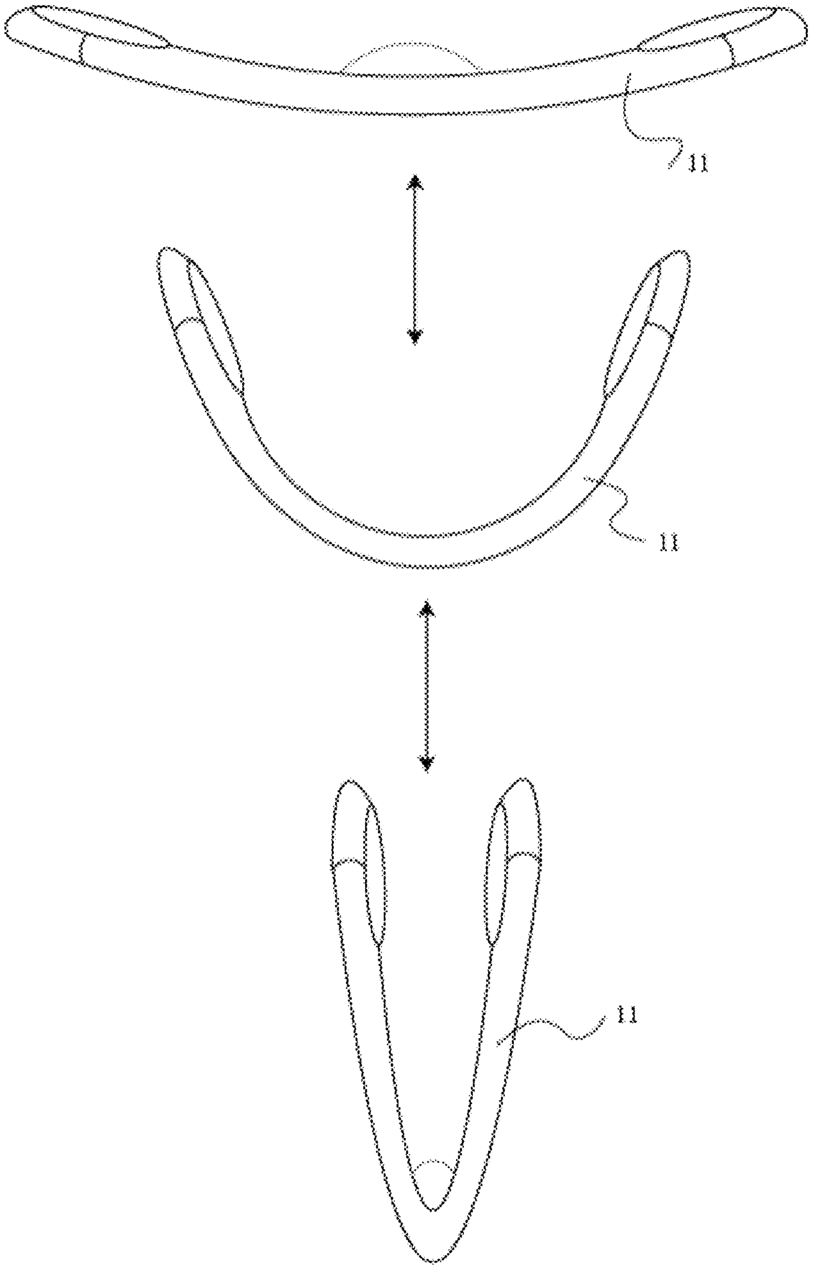
FIG. 13 is a schematic view showing a dilation angle range of the support member of the respiratory device and system according to an embodiment of the present disclosure.
Figure 27:
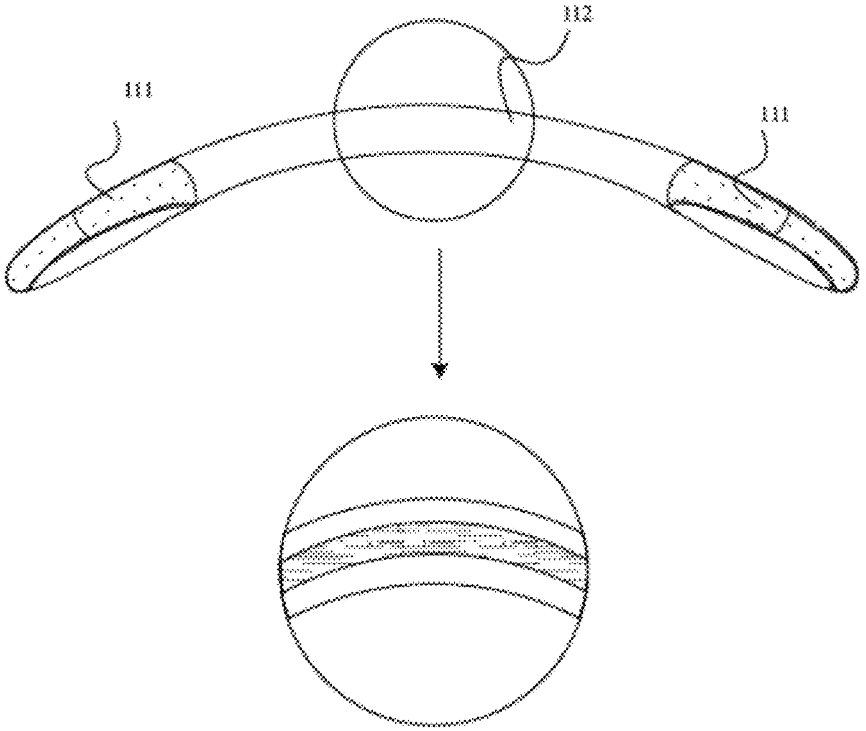
FIG. 27 is a cross-sectional view illustrating support members made of different materials in the respiratory device and system according to an embodiment of the present disclosure.

Specifically, this embodiment provides a nasal cavity dilation respiratory system 1, which is designed to achieve effective nasal cavity dilation while ensuring wearing comfort and stability through structural optimization and material selection. The nasal cavity dilation respiratory system 1 is configured to include a support member 11 and at least one connecting member 12, which are combined via a reliable, detachable connection. In this disclosure, the support member 11 is configured to be disposed adjacent to the user's nasal region and includes two end portions 111, an intermediate portion 112, and at least one attachment surface 113, which provides lateral support force for nasal cavity dilation during wearing. The support member 11 generally has a strip-shaped or sheet-like structure including two end portions 111 and an intermediate portion 112 connecting them. The overall structure of the support member 11 is designed to be symmetrical, in other embodiments, it may be asymmetrical. The two end portions 111 are respectively formed at opposite ends of the support member 11 and are curved naturally along the outer sides of the nasal alae to fit the contour of the nasal alae, improving fixation and preventing slippage. The intermediate portion 112 is disposed between the two end portions 111 and corresponds to the region between the nasal bridge and nasal tip when worn. The intermediate portion 112 may be arched, curved, or linear structure, so as to conform to the region between the nasal bridge and the nasal tip (as shown in FIGS. 8A, 8B, and 8C). In the arched configuration, the intermediate portion 112 is contoured to arch upward naturally, forming a relatively large contact area with the user's nasal bridge. The arch height is between 3 mm and 20 mm, and the arch radius is 20 mm to 60 mm (as shown in FIG. 8A), depending on the length of support member 11 (e.g., 30 mm radius for a 60 mm length). When worn, the arch transmits the pulling or outward force from the connecting members 12 evenly to the two end portions 111, which apply dilation force to the nasal wings in a soft and symmetrical manner. The arched structure is capable of self-supporting above the nasal bridge when the system is not under load. When worn, the support member generates an outward pulling force (as shown in FIG. 9). The central arch region, that is, the intermediate portion 112 of the support member 11, is configured to either contact or not contact the user's nasal bridge. When the central arch region is in contact with the nasal bridge, the reaction force generated is configured to be no greater than 20% of the total outward pulling force of the support member, thereby avoiding localized concentrated stress. In addition, the support member 11 may also adopt a curved structure, in which the intermediate portion 112 has a curvature design with a smoother continuous arc transition compared to the arched structure. The curvature radius is preferably between 25 mm and 80 mm (as shown in FIG. 8B), with a curvature of 0.1-0.01 $mm^{-1}$, adapted to facial surfaces of users having a nasal bridge curvature of 0.2 to 0.6 (dimensionless). The curved structure allows elastic deformation of approximately 5% to 30%, with maximum deflection not exceeding 15% of the support member length. In the linear structure, the intermediate portion 112 has a straight profile without noticeable curvature. It connects with the end portions 111 either at a fixed angle or directly, with a length of 20 mm to 60 mm and a total thickness of 0.5 mm to 20 mm (as shown in FIG. 8C). In this linear structure, external force is transmitted primarily along the central axis. The dilation force is applied from both ends and directly transmitted to the nasal ala region. The total length of the support member 11 in this embodiment ranges from 9 mm to 150 mm, with the intermediate portion 112 preferably between 30 mm and 80 mm. The thickness of the intermediate portion 112 is greater than or equal to that of the two end portions 111, and ranges from 1 mm to 15 mm. It may also feature a gradient thickness or local reinforcement. Specifically, the intermediate portion 112 can be molded to form a thickness that gradually transitions from the center to the ends during injection molding, or be locally thickened using secondary injection, thermal pressing, or material accumulation at key stress zones. In other implementations, the intermediate portion 112 is made of a flexible material with a thickness of 2 mm to 5 mm, balancing comfort and resilience. The intermediate portion 112 may be composed of the same or different material as the end portions 111. For example, it can be made of thermoplastic elastomers (TPE), thermoplastic polyurethane (TPU), or other flexible, biocompatible materials. It may also embed a metal sheet (e.g., stainless steel, aluminum alloy, shape memory alloy) or wire mesh (e.g., stainless steel mesh) to form a soft-outside, rigid-core structure that improves shape recovery and provides a defined dilation path. The support member 11 has a length range of 9 mm to 150 mm to accommodate facial sizes from children to adults (as shown in FIG. 10). For example, the support member 11 having a length of approximately 9-30 mm is defined as a short type, the support member 11 having a length of 60-120 mm is defined as a standard type, and the support member 11 having a length of about 150 mm is defined as a reinforced type. In specific applications, the short-type support member 11 is suitable for localized dilation, while the elongated support member 11 can cover a larger area and is suitable for scenarios such as continuous nighttime wear. The support member 11 has a uniform thickness, with at least a portion of its thickness falling within the range of 0.1 mm to 20 mm (as shown in FIG. 11). In other implementations, the support member 11 has a gradient thickness structure, in which different thickness distributions are provided either along its length (from one end portion 111 through the intermediate portion 112 to the other end portion 111) or along its width (in the crosswise direction of the nasal wing contact surface), so as to optimize local compliance and fit while maintaining overall strength (as shown in FIG. 12). Specifically, the thickness of the support member 11 may vary between different regions within a range of 0.1 mm to 20 mm. For example, the intermediate portion 112 may have a maximum thickness in an area d to carry the main dilation force and provide rigidity, while the end portions 111 taper to widths e and f, decreasing from d to f, reducing edge pressure and improving conformity to nasal curvature. The angle of the support member 11 is defined as the overall opening angle of the support member 11 in its worn state, specifically represented by the included angle between its two end portions 111 in space. This angle reflects the expansion angle range of the support member 11 when the system is worn, which is set between 30 degrees and 180 degrees (as shown in FIG. 13). Different angles determine the initial configuration of the support member 11 and the range of force application. When the angle of the support member 11 is set within the range of 30 degrees to 90 degrees, the support member 11 is in a pre-opened state and can naturally conform to the region from the nasal bridge to the nasal alae without imposing excessive load on the user. When the angle of the support member 11 is increased to a range of 90 degrees to 180 degrees, the support member 11 covers a wider nasal area, thereby accommodating users with a larger inter-alar distance and generating greater dilation force during wear. In other implementations, the angle of the support member 11 is configured to be within a range of 0 degrees to 180 degrees. When the angle of the support member 11 is set to 0 degrees, the two end portions 111 are structurally in a substantially overlapping or co-directional extended state, such that the entire support member 11 presents as a straight-line or folded-close configuration. This configuration is typically used in design schemes that require a compact form prior to wear for ease of storage and transportation, and is also applicable to deformable devices that are guided to expand by external connection members or by the user's own nasal structure. Specifically, the support member 11 is made of a rigid or semi-rigid material so as to ensure that it provides sufficient dilation support force and shape stability during wear. Preferred rigid materials include injection-molding-grade polycarbonate (PC) and acrylonitrile-butadiene-styrene copolymer (ABS), which possess excellent deformation resistance and structural rigidity, making them suitable for applications requiring a high degree of dilation amplitude and support strength. For semi-rigid materials, polypropylene (PP), polyurethane (PU), or ethylene-vinyl acetate copolymer (EVA) may be used. These materials maintain a certain degree of rigidity while retaining moderate flexibility, making them well-suited for conforming to complex nasal contours and providing a certain level of resilience. In certain structural designs, the support member 11 may further adopt a laminated structure (as shown in FIG. 27), for example, with an outer layer formed of high-rigidity materials such as polycarbonate (PC) or polyamide (PA) to enhance overall deformation control, and an inner layer formed of soft cushioning materials such as silicone, closed-cell foam, or textile materials to improve fit comfort and skin-friendliness during wear. The intermediate portion 112 and the end portions 111 may also be made of different materials, with the end portions 111 being softer and more deformable than the intermediate portion 112 to better conform to the skin. In other implementations, the support member 11 may be made of an elastomeric material (e.g., TPE or silicone rubber) to meet usage scenarios that require higher softness and comfort during wear.

Figure 14:
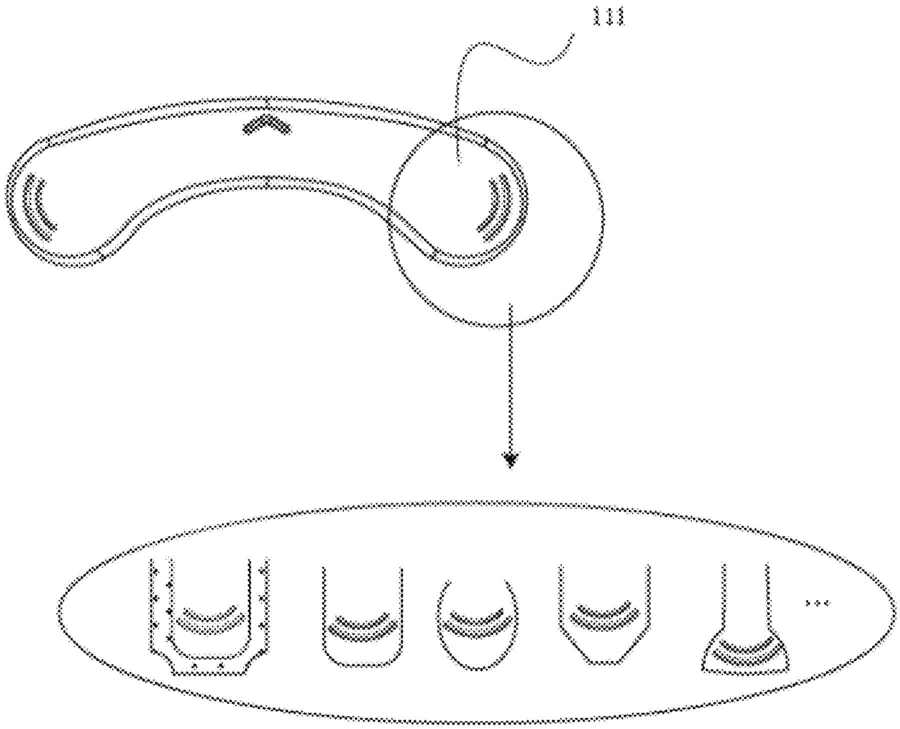
FIG. 14 is a schematic view showing different shapes of two end portions of the support member of the respiratory device and system according to an embodiment of the present disclosure.
Figure 28:
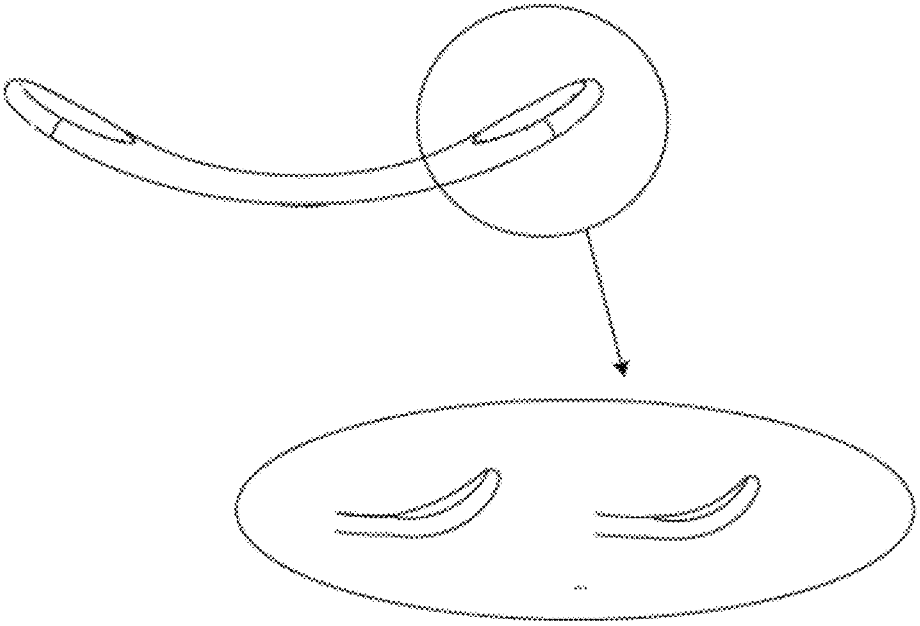
FIG. 28 is a schematic view showing different angles of the two end portions of the support member in the respiratory device and system according to an embodiment of the present disclosure.

The support member 11 includes two end portions 111, which are respectively formed at opposite ends of the support member 11. The two end portions 111 may be configured in various shapes, including elliptical, fan-shaped, angular, semi-annular, and other configurations (as shown in FIG. 14). For example, an elliptical end portion 111 can cover a wider contact area, making it suitable for users with broader or more rounded nasal alae; a fan-shaped end portion 111 provides an expanded contact region through gradually widening edges, suitable for nasal alae contours that are relatively flat or slightly curved; an angular end portion 111 provides a certain degree of lateral support, suitable for users with more defined nasal alae edges; and a semi-annular end portion 111 can partially encircle the nasal alae edge to achieve localized coverage and stable fixation. In addition, the two end portions 111 may be configured to form an arcuate bend of about 10 degrees to 30 degrees along both sides of the nasal wings (as shown in FIG. 28). In other implementations, the edges of the two end portions 111 may further be provided with rounded edges, chamfers, or soft edge wraps to prevent cutting pressure or indentation on the alae during wear. For example, a rounded-edge design mitigates local stress concentration through smooth edge transitions; a chamfered design effectively disperses stress via an angled transition; and a soft edge wrap may be formed by covering the edge of the end portion 111 with silicone or foam material to increase the soft contact area. The structure of the two end portions 111 may also include locally raised regions or flexible extension regions to alleviate concentrated stress on the alae. The raised region can enhance local support strength and prevent stability degradation caused by deformation of the support member 11 under load during wear; the flexible extension region may be realized through a gradient of hard and soft materials or localized film structures, enabling adaptive cushioning for the nasal wing skin, thereby mitigating concentrated stress and preventing redness, swelling, or discomfort from compression. In addition, the spatial arrangement of the two end portions 111 includes, but is not limited to, the following configurations: (1) a parallel configuration, in which the two end portions 111 are substantially parallel along the longitudinal direction of the support member 11, suitable for users with a narrow face or a small inter-ala distance; (2) an outwardly flared V-shaped configuration, in which the two end portions 111 open at a certain included angle, suitable for users with a wide face and laterally flared alae, effectively increasing lateral support force for the alae; and (3) a curved configuration, in which the support member 11 is made of rigid or semi-rigid material, and the two ends of the support member, in the absence of external force, exhibit a slight downward bend or drooping shape to fit the contour beneath the alae. Furthermore, the shape of the two end portions 111 may be configured to include, but is not limited to, arcuate shapes, slightly curved structures, hook-like structures, beveled shapes, thumb-shaped protrusions, rounded rectangles, or asymmetrical curved surfaces conforming to the ala contour. In other implementations, the two end portions 111 may be provided with cushioning layers whose thickness and shape correspond to the structure of the end portions 111. For example, flexible silicone gaskets or memory foam layers may be arranged on curved or hook-shaped end portions 111 to cushion contact pressure, enhance wearing comfort, and prevent slippage.

Figure 15:
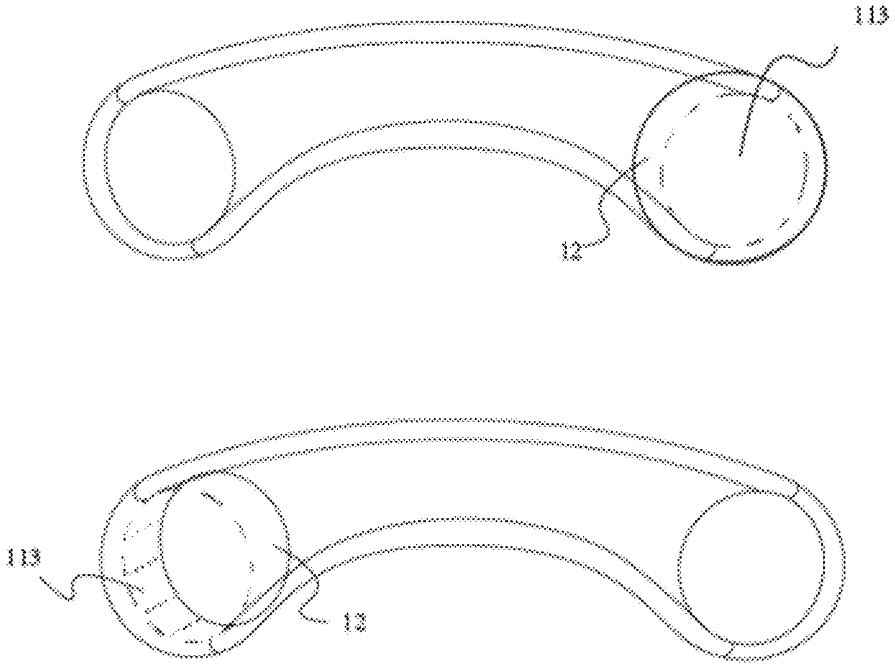
FIG. 15 is a schematic view showing an attachment surface having an area less than or equal to that of a second portion in the respiratory device and system according to an embodiment of the present disclosure.
Figure 16:
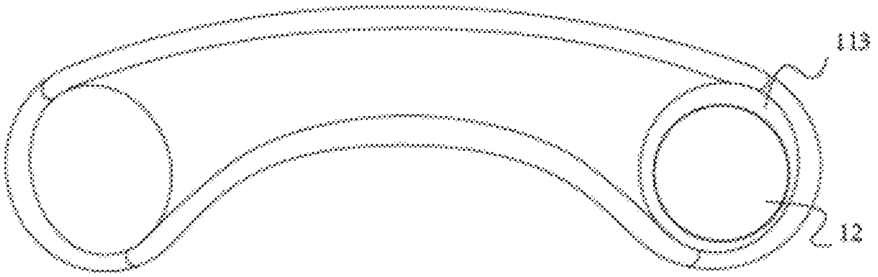
FIG. 16 is a schematic view showing the attachment surface having an area greater than that of the second portion in the respiratory device and system according to an embodiment of the present disclosure.
Figure 17:
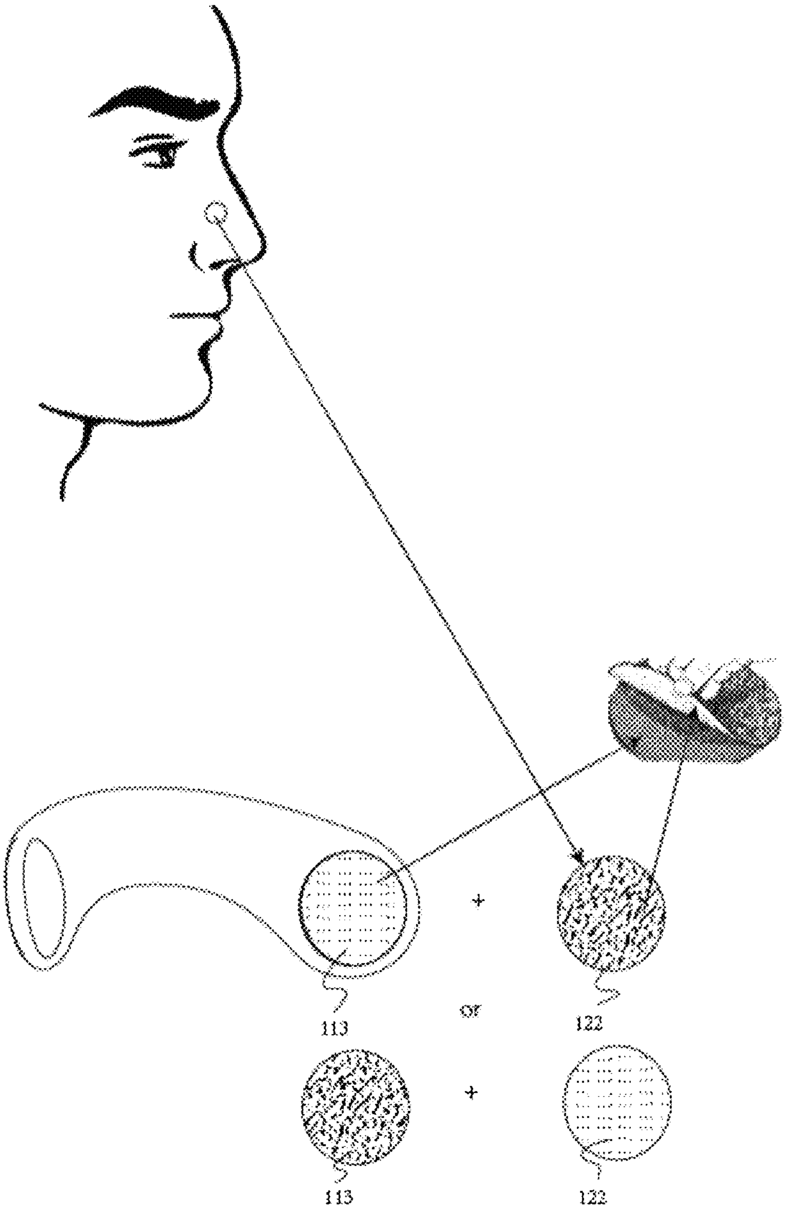
FIG. 17 is a schematic view showing the attachment surface and the second portion being connected via a hook-and-loop fastening structure in the respiratory device and system according to an embodiment of the present disclosure.
Figure 18:
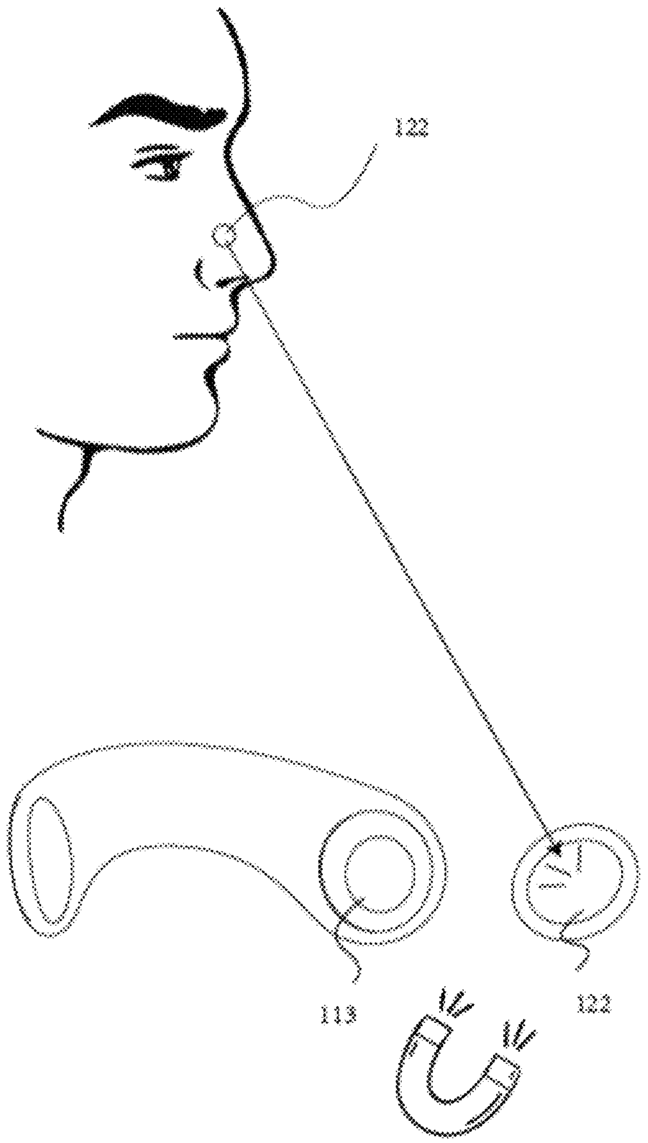
FIG. 18 is a schematic view showing the attachment surface and the second portion being connected via a magnetic structure in the respiratory device and system according to an embodiment of the present disclosure.

At least one attachment surface 113 is disposed on at least one surface of the end portion 111 of the support member 11 for connection to at least one connecting member 12. The at least one attachment surface 113 may adopt a hook surface, a loop surface, or a composite surface configuration (e.g., a portion being a hook surface and another portion being a loop surface) and is securely affixed to the end portion 111 of the support member 11 by means such as integrally molding, adhesive bonding, ultrasonic welding, thermal pressing, or stitching. Depending on the application requirements, the material of the attachment surface 113 may be selected from polyester, polyamide (PA), polyurethane, polyolefin, or composite materials thereof. These materials not only exhibit good mechanical strength and wear resistance but also maintain high attachment stability during repeated attachment and detachment cycles. The size of the attachment surface 113 is generally controlled within a range of 0.05 $cm^2$ to 20 $cm^2$ to balance sufficient connection area with wearing comfort. In at least one implementation, the area of the at least one attachment surface 113 is less than or equal to that of the second portion 122 (as shown in FIG. 15). In other implementations, the area of the at least one attachment surface 113 is greater than that of the second portion 122 (as shown in FIG. 16). The shape and size of the attachment surface 113 may be customized according to different nasal geometries and connecting member 12 configurations, with shapes including but not limited to circular, elliptical, polygonal, or irregular forms. In other implementations, the attachment surface 113 is configured to be directly integrated with the plastic substrate of the support member 11 via an integral molding process (e.g., injection molding). The joining process may include, but is not limited to, adhesive bonding, ultrasonic welding, thermal pressing, and stitched connection. In the present embodiment, the attachment surface 113 is disposed on the outer surface of both end portions 111 of the support member 11, i.e., closer to the user's nasal surface (as shown in FIG. 17), the attachment surface 113 adopts a hook-surface configuration, in which the surface is covered with micro-hook fibers such as polyamide (PA) or polypropylene (PP) fibers, configured to mate with the second portion 122 via hook-and-loop fasteners or buckles, thereby achieving secure connection and good reusability. Alternatively, the attachment surface 113 may adopt a loop-surface configuration, formed from flexible short fibers such as polyester (PET) or polyamide (PA), providing a soft, plush texture for mating with a hook-surface structure of the second portion 122 of the connecting member 12. In other implementations, the attachment surface 113 is configured to mate with other structures of the second portion 122, such as magnetic coupling or chemical adhesive bonding. For magnetic coupling, the attachment surface 113 may incorporate embedded magnetic sheets or metal plates (e.g., stainless-steel foils, nickel-plated iron sheets), while the second portion 122 is made of a magnetic material, thereby enabling magnetic attraction for quick assembly, disassembly, and daily cleaning (as shown in FIG. 18). When the attachment surface 113 is joined to the support member 11 by chemical adhesive bonding or hot-melt bonding, the attachment surface 113 may be made of materials with adhesive affinity, such as polyurethane (PU) or ethylene-vinyl acetate (EVA), and may be provided with micro-porous textures or guide grooves on its surface to enhance bonding strength and durability. In another implementation, the attachment surface 113 may be integrally formed with the support member 11 via an integral molding process, using materials including thermoplastic elastomers (TPE), thermoplastic polyurethane (TPU), polycarbonate (PC), or other compatible thermoplastic polymers. Additionally, the attachment surface 113 may be configured to connect to the support member 11 by means of a mechanical structure, such as plastic snap-fits, metal retaining rings, or elastic hooks. When mechanical coupling is employed, the attachment surface 113 may be pre-formed with structural features such as limit holes, positioning slots, mating protrusions, or flexible hanging loops to achieve a stable mechanical interlock connection.

Figure 19:
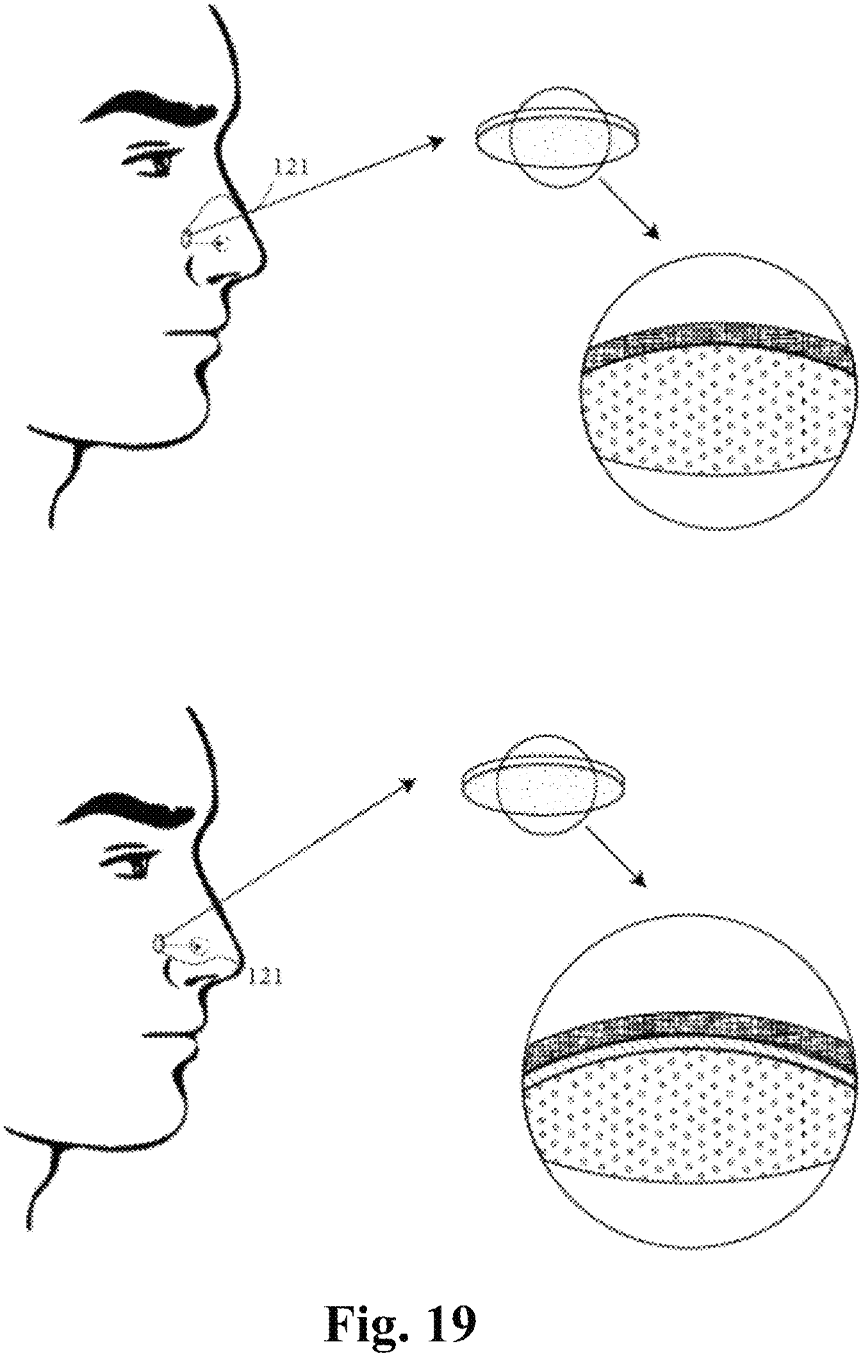
FIG. 19 is a schematic view showing a composite structure of a first portion of the respiratory device and system according to an embodiment of the present disclosure.
Figure 20:
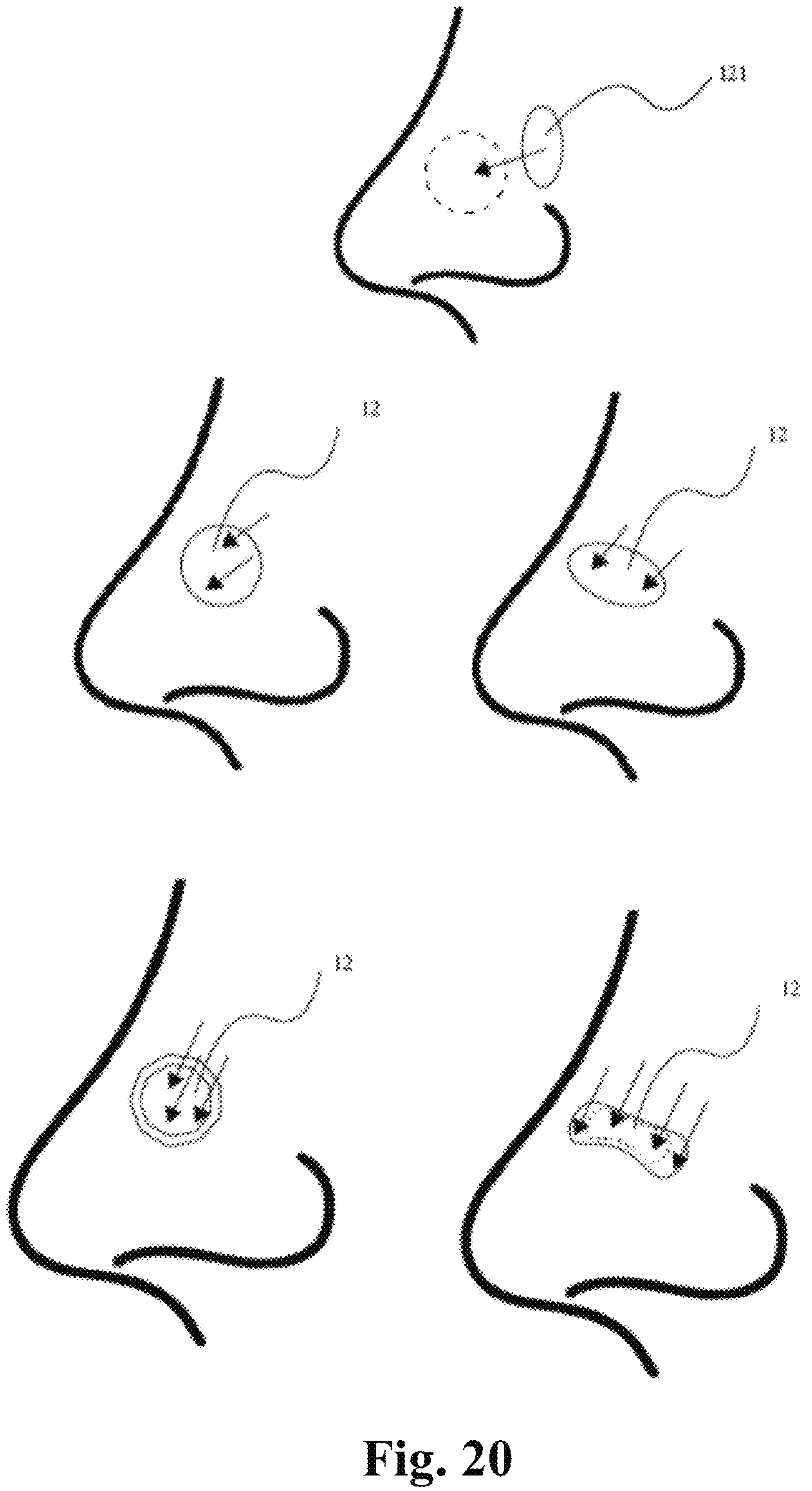
FIG. 20 is a schematic view showing different shapes of the first portion in the respiratory device and system according to an embodiment of the present disclosure.
Figure 21:
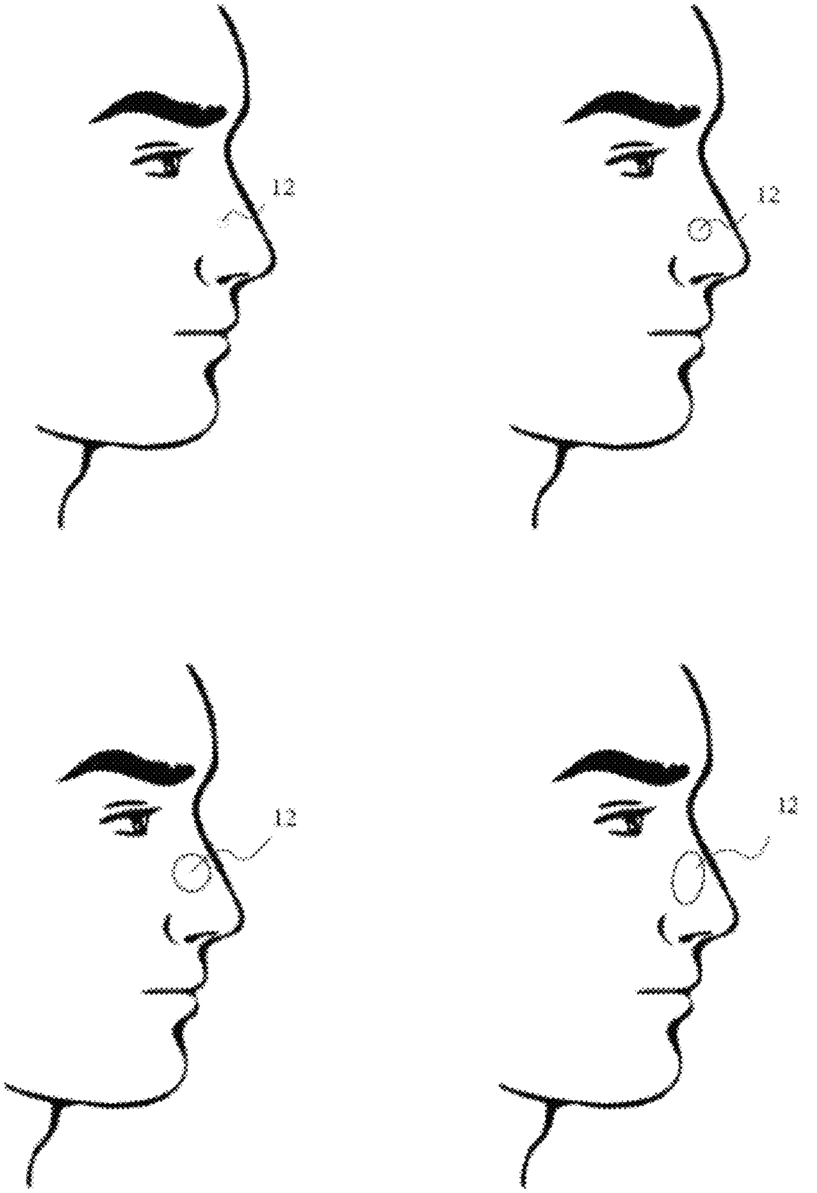
FIG. 21 is a schematic view showing a contact area of the first portion attached to the nose in the respiratory device and system according to an embodiment of the present disclosure.

In the detailed embodiments, the nasal cavity dilation respiratory system 1 includes at least one connector 12, which is configured to securely fasten the support member 11 to the lateral regions of the user's nose, ensuring that the support member 11 can effectively transmit the dilation force while providing a comfortable wearing experience. The at least one connector 12 generally includes a first portion 121 and a second portion 122, which respectively serve the functions of engaging with the nasal surface and connecting to the support member 11. The first portion 121 is configured to be at least partially affixed to the lateral regions of the user's nose, and is preferably made of a medical-grade skin-contact adhesive material having good breathability, skin compatibility, and hypoallergenic properties, thereby ensuring comfort and safety during prolonged wear. This portion may be in the form of a soft adhesive layer or a replaceable medical patch, facilitating convenient replacement and maintenance. Specifically, the first portion 121 of the at least one connector 12 is preferably made of environmentally friendly and reusable materials such as medical-grade silicone, thermoplastic elastomers (TPE), polyurethane films, and textile composite materials. Medical-grade silicone is soft, elastic, and highly biocompatible, enabling close conformity to the nasal skin while reducing irritation and indentations; it is also easy to clean and suitable for repeated use. Thermoplastic elastomers combine the softness of rubber with the processability of plastics, offering good skin-friendliness and durability, while also being recyclable. Polyurethane films are lightweight and breathable, feature waterproof and sweat-resistant properties, and are environmentally degradable, making them commonly used as the outer covering layer of adhesive materials. Textile composite materials integrate eco-friendly fibers such as organic cotton, bamboo fiber, or recycled polyester fibers to improve breathability and comfort while enhancing structural strength. In certain implementations, these materials are configured in a multilayer composite structure for the first portion 121, wherein the inner layer comprises medical-grade silicone or TPE serving as a skin-contact coating (as shown in FIG. 19). The intermediate layer may comprise textile composite materials or a film layer to enhance strength. The textile composite materials incorporate eco-friendly fibers such as organic cotton, bamboo fiber, or recycled polyester fibers, while the film layer is an ultra-thin, flexible polymer membrane—typically made of polyurethane or polyvinylidene fluoride—that offers waterproof and sweat-resistant properties, environmental degradability, and good breathability, and is commonly used as the outer covering layer of adhesive materials. The outer layer serves as a protective layer or a fixation layer, which is bonded to or mechanically connected with the second portion 122 of the connector 12 to achieve secure attachment and allow for cleaning and repeated use. In addition, the shape of the first portion 121 may be designed as circular, oval, polygonal, or irregular, according to the contour of the nasal alae, to accommodate the nasal features of different users and improve attachment stability (as shown in FIG. 20). In the present embodiment, the first portion 121 is configured in a circular structure, having a disk-like form with a diameter ranging from about 0.8 cm to 4 cm, made of a flexible medical adhesive material, enabling even distribution of adhesion force after attachment. In other implementations, the first portion 121 may have an oval structure with the major axis extending along the user's nasal ala, particularly suitable for users with wider nasal alae or a larger outer skin area. This structure provides a greater contact area, typically with a major axis of 2.0 to 3.5 cm and a minor axis of 1.0 to 2.0 cm, enabling more secure coverage of the nasal ala surface and improved fixation. The first portion 121 may also be configured in polygonal shapes, such as hexagons or octagons, which offer greater structural strength through regular boundaries, suitable for usage scenarios requiring stronger tensile support. The corners may be designed with rounded transitions to avoid scratching the skin, ensuring both conformability and durability. Furthermore, the first portion 121 may be formed in an irregular shape, customized based on three-dimensional data of the nasal ala contour, such as an asymmetrical structure with local depressions or protrusions, suitable for special user groups with high requirements for fit and significant differences in facial morphology. The contact area of the first portion with the nose is generally controlled within the range of 0.05 $cm^2$ to 20 $cm^2$ to balance fixation strength and skin load (as shown in FIG. 21). Different shapes of the first portion correspond to different contact area ranges, thereby enabling targeted support and adhesion force adjustment for different regions of the user's nasal alae. The size and shape will affect the contact area, which in turn influences adhesion strength and skin sensation (as shown in FIG. 20).

Figure 22:
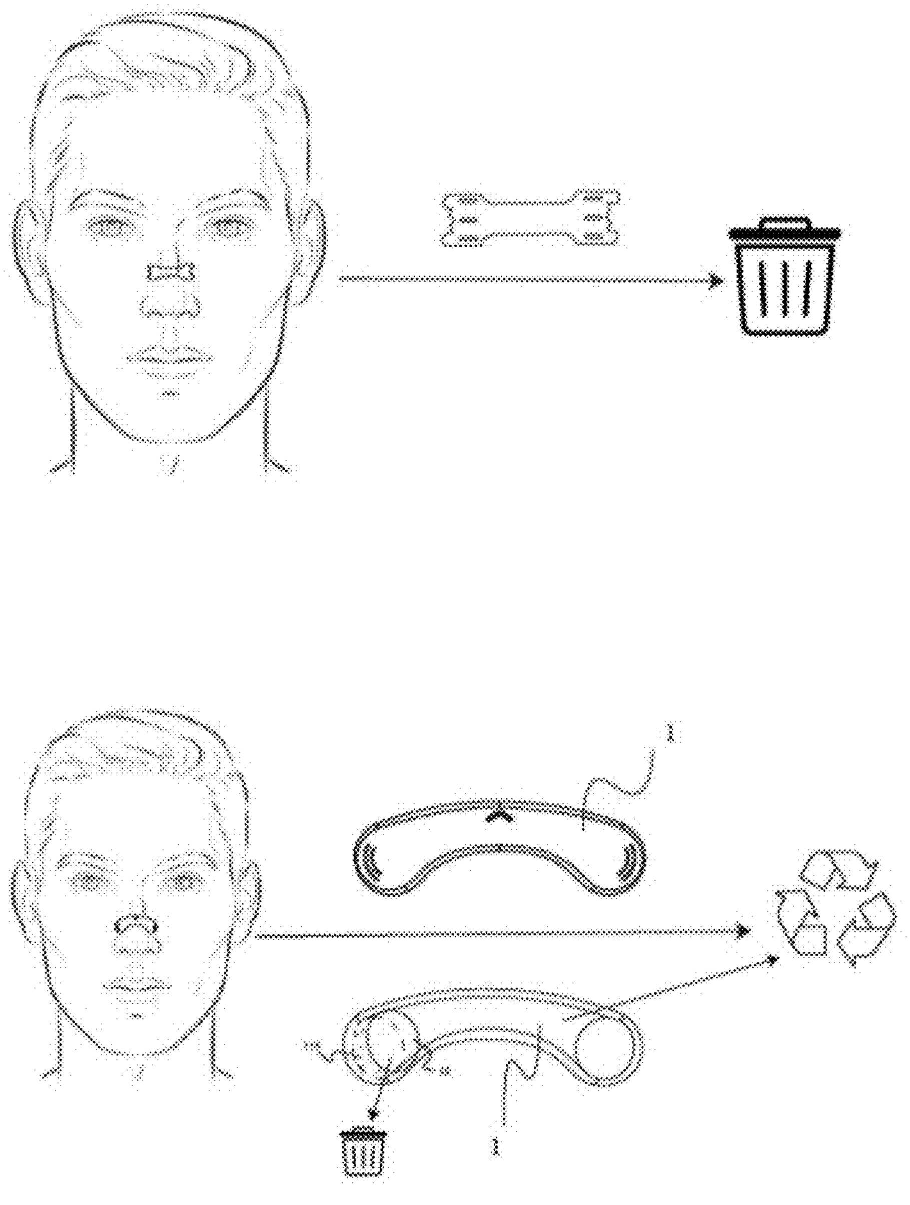
FIG. 22 is a schematic view illustrating a reusability of the respiratory device and system according to an embodiment of the present disclosure.
Figure 23:
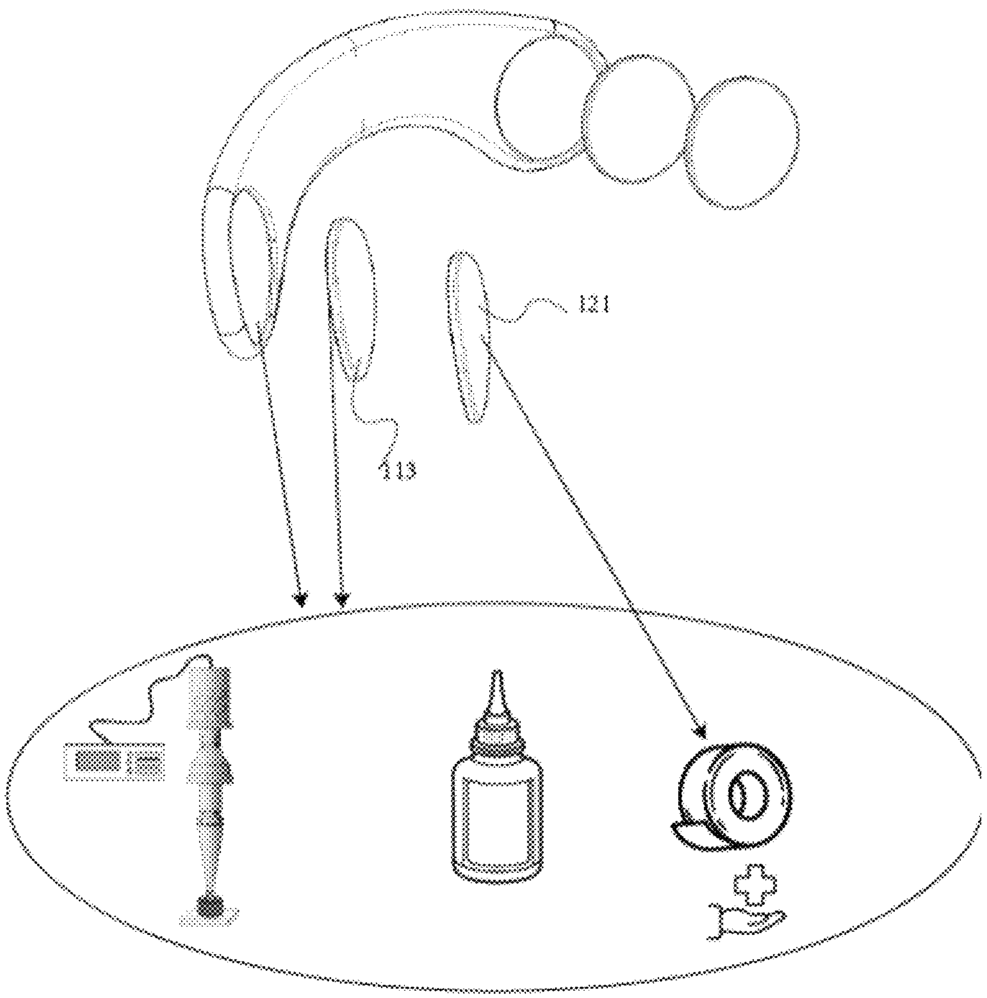
FIG. 23 is a schematic diagram illustrating connection methods for the attachment surface and the first portion of the respiratory device and system in an embodiment of the present disclosure.

The second portion 122 is configured to be detachably connected to at least one attachment surface 113 of the support member 11, thereby enabling convenient assembly and disassembly of the connector 12 and the support member 11. The respiratory system 1 adopts a modular, detachable structural design, which differs from disposable patch-type dilators and satisfies the requirement for reusability (as shown in FIG. 22). The connector 12 is configured to be connected to the support member 11 using any one of adhesive bonding, hook-and-loop fastening, mechanical coupling, magnetic attraction, or buckle connection, or any combination thereof. The second portion 122 and the at least one attachment surface 113 adopt a hook-and-loop fastening structure, which includes a hook surface and a loop surface. In one implementation, the hook surface is provided on the second portion 122 of the connector 12, while the loop surface or a corresponding mating structure is provided on the attachment surface 113 of the support member 11. This configuration facilitates quick engagement during wearing by simple pressing, while also providing high operational convenience during detachment. The hook-and-loop structure may be made of polyamide (PA), polyester, polyamide (PA)-polyester blends, TPU-laminated polyamide (PA), brushed fabric materials, or polypropylene thermo-formed hooks, offering good reusability, soft skin contact, and stable adhesion. In another implementation, the arrangement may be reversed, with the loop surface provided on the second portion 122 of the connector 12, and the hook surface provided on the attachment surface 113 of the support member 11. This design is particularly suitable when the support member 11 is made of a rigid or semi-rigid structure, as its stronger surface support capacity allows the hook surface structure to be fixed more securely, thereby enhancing overall wearing stability and service life during use. Both of the above configurations can meet the requirements of easy assembly/disassembly, adjustable strength, and reusability, and the choice can be flexibly made in practical applications according to the product design objectives and manufacturing convenience. The hook surface material may be selected from polyamide (PA), polypropylene (PP), polyethylene (PE), polyester (PET), thermoplastic polyurethane (TPU), and other materials, which possess good elastic recovery, wear resistance, and structural strength. Recycled polyamide (PA) and other eco-friendly materials may also be used to achieve green design. The loop surface portion is typically made of materials such as polyester fibers, polyamide (PA) fibers, polyester-cotton blends, nonwoven fabrics, or flocked layers, featuring softness, skin-friendliness, tear resistance, and ease of processing. Some high-end products may further adopt bio-based polymers such as polylactic acid (PLA) to enhance biodegradability and sustainability. The buckle structure enables mechanical, repeatable attachment between at least one connector 12 and the support member 11, allowing the user to conveniently detach and replace the connector 12 or adjust the position of the support member 11 as needed, while ensuring stability during wear. The bonding strength of the buckle can be controlled by adjusting the hook-and-loop (buckle) area, thereby setting the connection force between the connector 12 and the support member 11 within a range of 2 gf to 200 gf. The tension of the intermediate portion 112 of the support member 11 is less than or equal to the connection force between the connector 12 and the support member 11, ensuring that the attachment is neither excessively tight, which could cause discomfort, nor too loose, which could lead to detachment. In addition to hook-and-loop fasteners, the buckle may also take the form of polyamide (PA) buckles, plastic snaps, metal rings, or elastic hooks, all of which utilize a physical latching principle to achieve both stability and detachability in the connection. In other implementations, the second portion 122 may also be connected to the attachment surface 113 of the support member 11 by means of magnetic attachment, chemical adhesive bonding, or hot-melt bonding. The magnetic attachment structure uses embedded magnets to achieve quick adsorption and detachment, facilitating frequent replacement or cleaning of the device. Magnetic materials such as neodymium-iron-boron or soft magnetic alloys can ensure sufficient magnetic force and durability. Chemical adhesive bonding and hot-melt bonding are suitable for long-term wearing scenarios that require high connection stability. Common adhesives include medical-grade acrylic adhesives, silicone adhesives, and hot-melt adhesives, which can achieve firm bonding on surfaces of different materials. The integrally formed structure achieves a seamless connection between the connecting portion and the support member 11 through overall injection molding, hot pressing, or co-extrusion processes, thereby improving overall strength, aesthetics, and resistance to water and dust. The connection force generated between the support member 11 and at least one connector 12 is within the range of 2 gf to 200 gf. A flexible transition structure, such as a soft connecting strap or elastic cord, may also be provided between the first portion 121 and the second portion 122 of at least one connector 12 to improve flexibility and comfort during wear, while reducing localized stress on the skin of the nose. At the same time, the material selection for at least one connector 12 shall meet medical safety standards, and be resistant to sweat, oils, and bacteria to ensure hygiene. In addition, at least one connector 12 may be configured with an adjustment mechanism, such as a hook-and-loop adjustment strap, a micro-adjustment fastener, or an elastic component, to enable personalized adjustment of wearing tightness, further improving stability and user experience. In a hook-and-loop structure, the connection strength can be flexibly adjusted by changing the contact area between the hook surface and the loop surface, thereby achieving different levels of adhesion and fixation force, effectively balancing stability and ease of detachment. A micro-adjustment fastener can precisely control connection length or tension through mechanical sliding or locking, allowing the user to quickly adjust according to actual needs. Elastic components, such as elastic cords or elastic bands, provide flexible tension, reduce localized pressure during wearing, and enhance comfort. The respiratory system 1 applies appropriate tensile force to both ends of the support member 11 via at least one connector 12 to achieve effective dilation of the nasal alar. The dilation magnitude is adjustable within the range of 0.1 mm to 20 mm. For example, if the distance between the two sides of the nasal alar after dilation is a, and the distance before expansion is b, the dilation magnitude is a-b (as shown in FIG. 9). This structure balances flexibility and stability, reduces compression on the nasal soft tissue, and ensures comfort and safety during wear.

Figure 24:
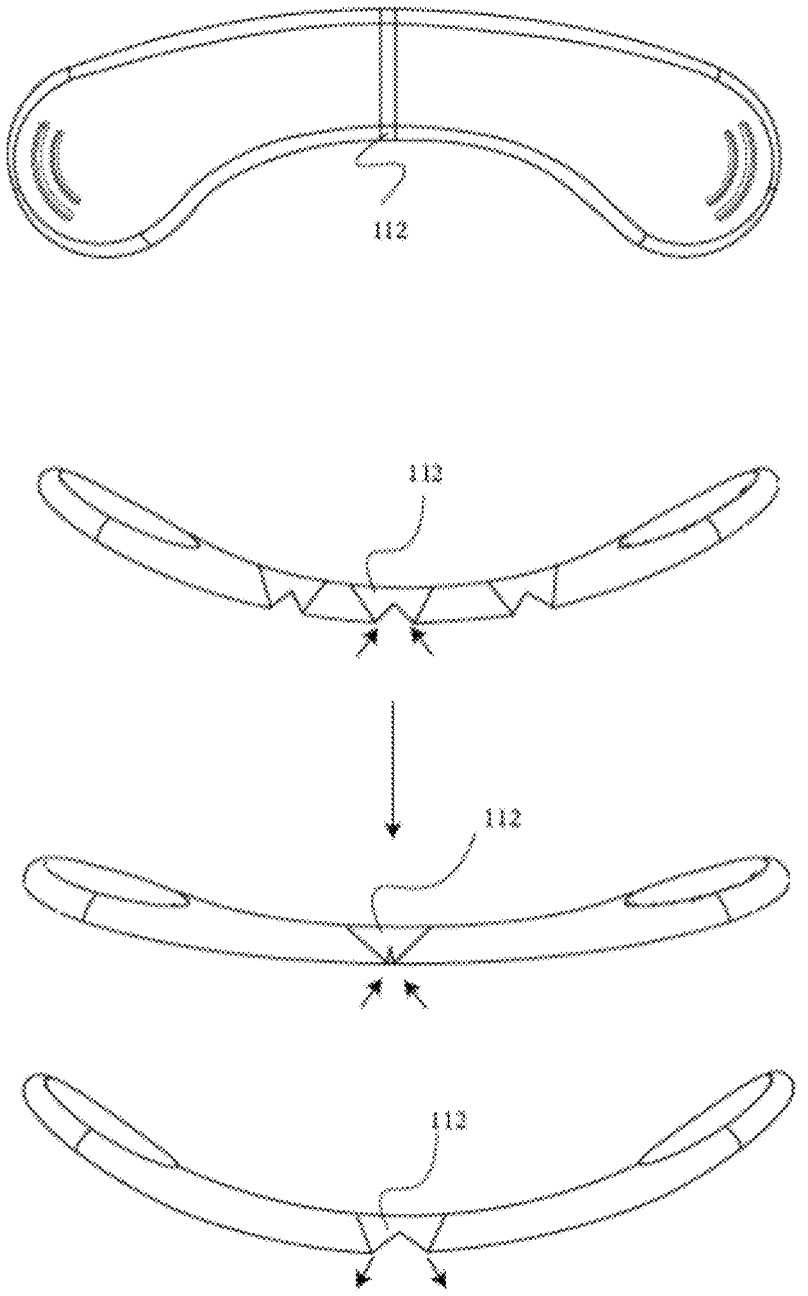
FIG. 24 is a schematic view illustrating a serrated structure formed on the intermediate portion of the respiratory device according to an embodiment of the present disclosure.

In some other implementations, the intermediate portion 112 is provided with a serrated structure (as shown in FIG. 24).

Figure 26:
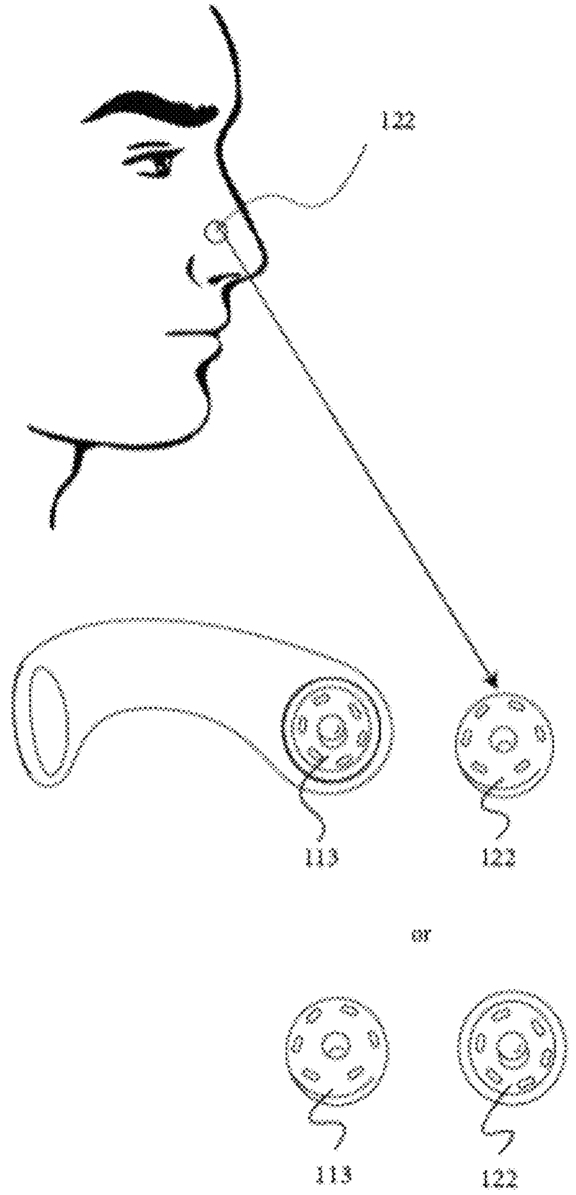
FIG. 26 is a schematic diagram illustrating the respiratory device in which the attachment surface and a connecting member are connected via a mechanical snap-fit structure.

In some other implementations, at least one connector 12 employs a mechanical snap-fit structure for connection with the support member 11 (as shown in FIG. 26).

Figure 25:
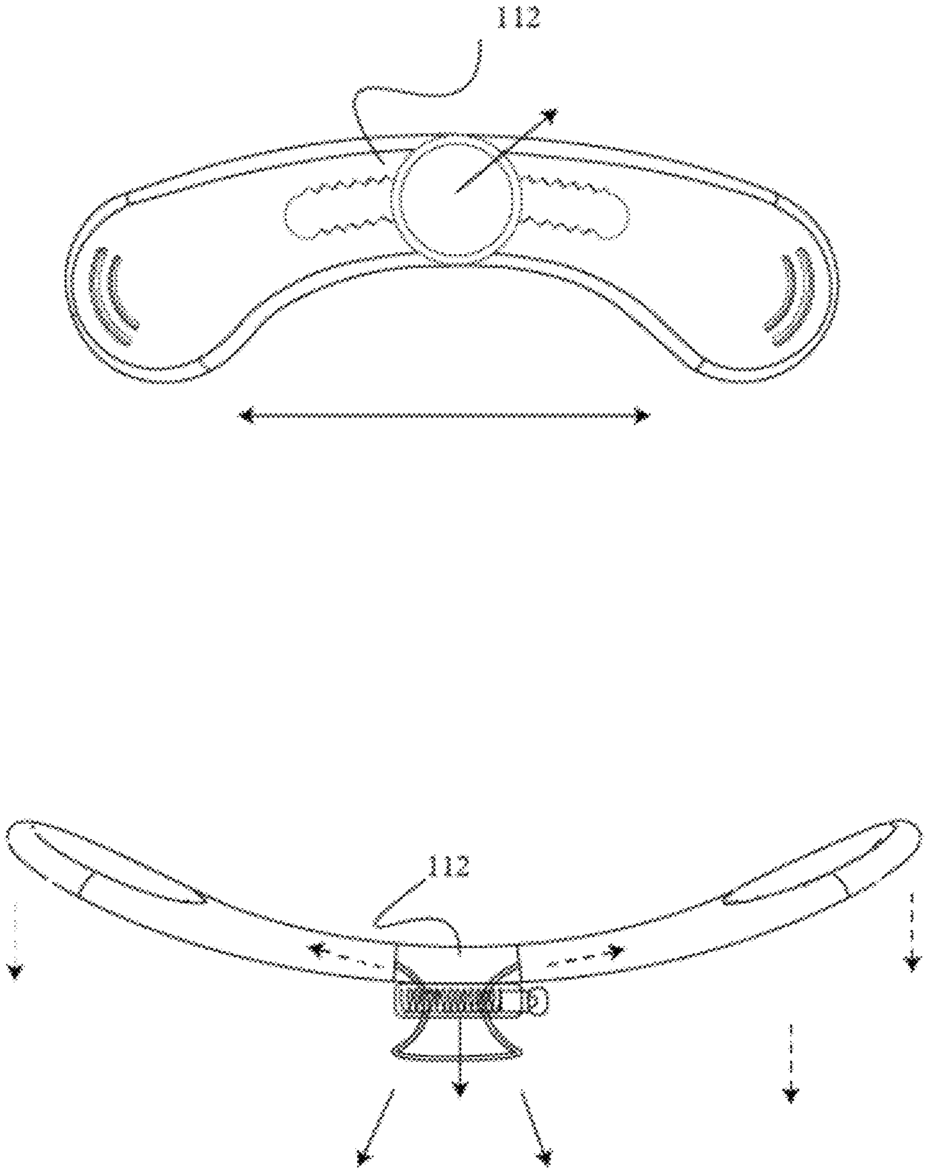
FIG. 25 is a schematic view illustrating an autonomously adjustable mechanism of the respiratory device according to an embodiment of the present disclosure.

In some other implementations, the respiratory system 1 is configured to allow self-adjustment of the dilation angle and dilation force (as shown in FIG. 25).

Embodiment 2

The respiratory system 1 of the present embodiment includes: a support member 11 configured to be disposed in a region adjacent to the user's nasal area, the support member 11 including two end portions 111, an intermediate portion 112, and at least one attachment surface 113; the two end portions 111 are respectively formed at opposite ends of the support member 11; the intermediate portion 112 is disposed between the two end portions 111 and is configured to correspond, when worn, to the region between the user's nasal bridge and nasal tip; at least one attachment surface 113 is configured to be provided on at least one surface of the end portion 111 for connection with at least one connector 12; and at least one connector 12, the at least one connector 12 including a first portion 121 and a second portion 122, wherein the first portion 121 is configured to be at least partially attached to regions on both sides of the user's nasal area, and the second portion 122 is configured to connect with the attachment surface 113 to removably couple the support member 11 and the at least one connector 12.

The difference between the present embodiment and Embodiment 1 lies in that the intermediate portion 112 of the support member 11 is configured with a serrated structure. The serrated structure is continuously arranged along the length direction of the intermediate portion 112, forming a plurality of alternating bends, which may be acute, right, or obtuse angles, so that the intermediate portion 112 has a compliant structural form capable of better conforming to deformation under external force. By means of localized thinning or geometric shaping, the serrated structure allows the intermediate portion 112 to bend more flexibly and adjust its shape when subjected to force, thereby enabling the support member 11 to better conform to the curvature of the user's nose and enhancing wearing comfort and stability. In addition, the serrated structure can effectively distribute and cushion pressure on the nasal bridge area, reducing the localized pressing sensation caused by a rigid support member 11 and minimizing user discomfort. The size, depth, and angle of the serrations may be adjusted according to different application needs, with thickness generally controlled within the range of 0.1 mm to 5 mm to balance sufficient support strength with good flexibility. Through this serrated structure design, the intermediate portion 112 of the support member 11 not only achieves structural compliance but also enhances protection of the nasal bridge area, meeting the wearing needs of users with different nasal shapes. This structure is particularly suitable for support members 11 made of semi-rigid materials, thermoplastic elastomers, or shape-memory polymers, allowing the support member 11 to maintain the necessary dilation force while flexibly adjusting its form to fit various nasal contours. The serrated design is also amenable to manufacturing processes such as laser cutting, die-cutting, or stamping, ensuring production efficiency and product consistency. By providing the intermediate portion 112 of the support member 11 with a serrated structure, the present embodiment offers a nasal dilation solution that is both comfortable and practical.

Moreover, the technical characteristics described in the above implementations may be combined as needed to obtain a respiratory system 1 incorporating all or part of the foregoing characteristics.

Embodiment 3

The respiratory system 1 of the present embodiment includes: a support member 11 configured to be positioned adjacent to a user's nasal region, the support member 11 including two end portions 111, an intermediate portion 112, and at least one attachment surface 113; the two end portions 111 are respectively formed at opposite ends of the support member 11; the intermediate portion 112 is disposed between the two end portions 111 and configured to correspond, when worn, to the area between the user's nasal bridge and nasal tip; the at least one attachment surface 113 is configured on at least one surface of the end portion 111 for connection with at least one connector 12; the at least one connector 12 includes a first portion 121 and a second portion 122, the first portion 121 being configured to be at least partially attached to lateral regions of the user's nose, and the second portion 122 being configured to connect with the attachment surface 113 so as to detachably connect the support member 11 to the at least one connector 12.

The distinction between the present embodiment and Embodiment 1 is that the respiratory system 1 is configured to allow autonomous adjustment of the dilation angle and dilation force to meet different users' personalized requirements for comfort and performance. The intermediate portion 112 of the respiratory system 1 is provided with an adjustable structure, for example, by incorporating movable folding joints, sliding slots, or elastic stretch zones (as shown in FIG. 25), enabling the user to manually or automatically adjust the opening angle between the two ends according to their nasal anatomy, thereby controlling the dilation force applied to the nasal cavity.

In the present embodiment, the intermediate portion 112 of the support member 11 is provided with a serrated structure, and a buckle is disposed externally on the intermediate portion 112, configured such that pulling the buckle outward adjusts the length of the support member 11, and pressing the buckle secures the length of the support member 11 (as shown in FIG. 25). In specific implementations, the intermediate portion 112 of the support member 11 may adopt a segmented design, with each segment connected via flexible connectors or hinge mechanisms, allowing rotation or bending within a defined range. Through rotational adjustment or a preset detent mechanism, the user can adjust the angle of the support member 11 from a smaller closed position to a larger open position, with the angle generally set between 0° and 150° to accommodate different nasal shapes and comfort requirements. At the same time, the support member 11 may also incorporate elastic materials or spring elements to provide adjustable elastic restoring force. While adjusting the angle, the adjustable structure delivers a corresponding dilation force, adjustable within a range of 2 gf to 200 gf, ensuring sufficient support during nasal dilation while avoiding excessive pressure that may cause discomfort. Furthermore, the device may be equipped with mechanical adjustment mechanisms, such as a micro-adjustment knob, slider, or hook-and-loop adjustment strap, enabling the user to adjust the expansion angle and force at any time during wear, thus achieving dynamic adjustment.

Embodiment 4

The respiratory system 1 of the present embodiment includes: a support member 11 configured to be positioned adjacent to a user's nasal region, the support member 11 including two end portions 111, an intermediate portion 112, and at least one attachment surface 113; the two end portions 111 are respectively formed at opposite ends of the support member 11; the intermediate portion 112 is disposed between the two end portions 111 and configured to correspond, when worn, to the area between the user's nasal bridge and nasal tip; the at least one attachment surface 113 is configured on at least one surface of the end portion 111 for connection with at least one connector 12; the at least one connector 12 includes a first portion 121 and a second portion 122, the first portion 121 being configured to be at least partially attached to lateral regions of the user's nose, and the second portion 122 being configured to connect with the attachment surface 113 so as to detachably connect the support member 11 to the at least one connector 12.

The distinction between the present embodiment and Embodiment 1 is that the at least one connector 12 adopts a mechanical snap-fit structure as the means of connection with the support member 11 (as shown in FIG. 26). Specifically, the attachment surface 113 is configured with a concave bayonet structure having an annular engagement groove, while the second portion 122 is configured with a corresponding convex snap-fit portion including a central protrusion and an outer elastic locking ring. When pressed, the convex snap-fit portion is inserted into the bayonet of the attachment surface 113 and securely engages with the annular groove. Conversely, the convex snap-fit portion may be provided on the end portion 111 of the support member 11, with the concave bayonet structure provided on the second portion 122 of the connector 12. The mechanical snap-fit structure requires no adhesive or hook-and-loop assistance, allowing one-handed assembly and disassembly, making it suitable for scenarios requiring frequent replacement or cleaning. The mechanical snap-fit structure may be made from medical-grade materials with toughness and elasticity, such as polyamide (PA), polycarbonate (PC), or acrylonitrile butadiene-styrene (ABS), ensuring good deformation capability and durability. In other implementations, stainless steel or aluminum alloys may be used to provide higher strength and reusability, accommodating different wearing requirements and operational scenarios. In the worn state, the snap-fit structure maintains the relative position between the connector 12 and the support member 11, providing sufficient resistance against detachment during facial movements, thereby ensuring the overall wearing stability and dilation effectiveness of the device.

The nasal dilation respiratory device and system of the present disclosure offers at least the following beneficial effects:

Conventional nasal dilation products are generally categorized into two types: disposable adhesive-type dilators and integrated molded-structure dilators. Disposable adhesive-type dilators typically suffer from issues such as simple structure, weak dilation force, poor adaptability, and high usage cost. On one hand, most disposable adhesive-type dilators rely primarily on skin adhesion for fixation, lacking a stable support component in their structure, and generating only limited outward pulling force on the nasal alar region via thin films or elastic fibers applied externally. Since the adhesion force is easily affected by factors such as perspiration, skin oils, and skin type, the adhesive strip is prone to displacement, edge lifting, or detachment during use, thereby impairing dilation performance. Furthermore, as conventional adhesive strips are generally made of low-cost materials intended for single use, their elasticity and structural strength are insufficient to sustain effective dilation over time; fatigue deformation often occurs after only a few hours, leading to a gradual reduction in dilation effect. In addition, such adhesive strips are usually of standard size and lack adjustment mechanisms for different nasal geometries. For users with higher nasal bridges or wider nasal alar spacing, the fit and wearing experience are often unsatisfactory. The respiratory system of the present disclosure effectively addresses the above problems. It adopts a "support member 11+at least one connector 12" modular combination, wherein the support member 11 provides stable and directional nasal cavity dilation force—adjustable in size and angular deformation—significantly greater than that of conventional adhesive strips, thereby improving breathing patency. The at least one connector 12 is partially made of soft, skin-friendly materials with selectable attachment area, not only improving wearing comfort but also achieving firm connection to the support member 11 via hook-and-loop fastening, thereby ensuring strong adaptability, structural stability, and resistance to detachment during prolonged wear. Additionally, the support member 11 is reusable, requiring only the replacement of the at least one connector 12, which reduces long-term usage costs, minimizes material waste, and improves environmental sustainability. Therefore, in terms of dilation performance, comfort, structural stability, adaptability, and cost-effectiveness, the respiratory system of the present disclosure offers significant technical advantages over conventional products—particularly excelling in use cases such as daily breathing improvement and sustained dilation during physical activity—providing a high-performance alternative to traditional nasal dilation devices.

In recent years, certain nasal dilation products have attempted to incorporate magnetic attachment structures in an effort to achieve component detachability and structural simplification. However, while magnetic structures offer some convenience in modular assembly, they present several non-negligible drawbacks in practical applications—particularly in terms of safety, material biocompatibility, cost control, and manufacturing complexity. From a safety standpoint, magnets are small, rigid components, especially in the form of miniature magnetic plates used for coupling the at least one connector 12. During use, these components are prone to detachment due to friction, impact, or improper handling by the user. In unconscious scenarios such as sleep or physical activity, accidental inhalation into the nasal cavity or oral cavity could lead to serious medical consequences, including choking, ingestion of foreign objects, or gastrointestinal obstruction—posing high-risk hazards. Such potential dangers are especially severe for sensitive user groups such as infants and elderly individuals. From a materials and biocompatibility perspective, magnets often contain metal alloys such as neodymium-iron-boron. Some users are sensitive to metals, and those with implanted medical devices such as pacemakers or hearing aids must avoid magnetic field interference, further limiting usage. In contrast, the structure of the present disclosure employs hook-and-loop fastening without any metal components, utilizing flexible, low-allergen materials that minimize skin irritation and accommodate a wide range of users. Furthermore, the magnetic connection force is non-adjustable, which may result in attachment forces that are either too weak—leading to detachment—or too strong—making removal difficult and potentially causing skin pinching injuries. Hook-and-loop fastening, by contrast, allows the bonding strength to be personalized through adjustment of the contact area and engagement angle, resulting in more flexible and stable structural connections. From a manufacturing and cost-control standpoint, magnetic structures require complex processes such as directional installation, encapsulation, and embedding, which drive up production costs and make it difficult to maintain high process yield rates. By comparison, hook-and-loop fasteners are mature, widely used industrial components that can be directly assembled with the modules of the at least one connector 12 and the support member 11. They have low procurement costs, moderate processing precision requirements, and are well-suited for standardized mass production, thereby achieving higher overall manufacturing efficiency. Accordingly, compared with magnet-based products, the structure provided by the present disclosure offers significant advantages in safety, adaptability, comfort, cost control, and production efficiency. It is particularly well-suited for daily, continuous-wear nasal dilation applications that require a sensation-free, safe, and controllable design, while being user- and environmentally friendly, reducing the user's cost of use and medical burden.

In existing nasal dilation products, integrated structural designs are relatively common. Such products typically combine the fixing structure, the dilation support member 11, and the attachment portion into a single unit, aiming to simplify both operational steps and structural form. However, in practical use, integrated structures reveal several core issues. The first is functional conflict: the dilation structure requires sufficient rigidity to expand the nasal cavity, while the attachment portion must have a certain softness to ensure wearing comfort. In an integrated design, these two functions cannot be separated, often resulting in a situation where the user cannot achieve the desired dilation effect and, at the same time, experiences nasal alar compression, friction, or even skin injury due to the rigid material. The second issue is the lack of adjustability: integrated structures cannot easily adapt to variations in users' nasal anatomy, especially in nasal alar width and nasal bridge height. Significant individual differences may lead to inadequate dilation angles or poor positioning of the integrated dilator, reducing user comfort. In the present disclosure, the nasal dilation respiratory system adopts a modular concept, separating the functions of "dilation force output" and "attachment fixation." This is achieved through a "support member 11+at least one connector 12" configuration that assigns functions to dedicated components. The support member 11 is made from adjustable materials, with its thickness, length, and curvature all customizable or adjustable to the user's needs. The support member 11 provides a stable outward dilation force through deformation without compromising the flexible attachment performance of at least one connector 12. At least one connector 12 is made from soft, hypoallergenic materials with good skin compatibility and has an adjustable contact area to match different nasal anatomies, improving the wearing experience. The structure employs hook-and-loop fastening, enabling repeated attachment and detachment while providing high bonding strength and preventing detachment during use, ensuring stability throughout wear. Compared with traditional integrated structures, this modular design significantly enhances product adaptability, stability of dilation force, and wearing comfort, transforming nasal dilation devices from a "universal" type to a "personalized" type. Moreover, the modular configuration facilitates manufacturing process standardization and quality control of individual modules, improving production efficiency and product consistency. From the perspectives of structural-functional separation, enhanced user experience, individual adaptability, and manufacturing optimization, the present disclosure offers comprehensive advantages over conventional integrated dilation products. It represents a significant optimization and practical advancement in the design concept of nasal dilation systems.

The technical features described in the implementations above can be combined in any manner. To maintain concise description, not all possible combinations of features from the above implementations are described in detail; however, as long as there is no conflict among these feature combinations, they should be considered within the scope of the present disclosure.

The embodiments described above merely illustrate several possible implementations of the present disclosure in a more specific and detailed manner and should not be construed as limiting the scope of the claimed invention. It should be noted that, for those skilled in the art, various modifications and improvements can be made without departing from the inventive concept of the disclosure, and such modifications and improvements should fall within the protection scope of the present disclosure. Accordingly, the protection scope of the present disclosure should be defined by the appended claims.

It must be noted that as used herein and in the appended claims, the singular forms “a”, “an”, and “the” include their plural equivalents, unless the context clearly dictates otherwise.

The invention claimed is:

1. A nasal dilation respiratory device configured to be attached to a user’s nose to dilate a nasal cavity, comprising:

a support member configured to be provided adjacent to a nasal region of the user, the support member comprising two end portions, an intermediate portion, and at least one attachment surface;

wherein the two end portions are respectively formed at opposite ends of the support member;

wherein the intermediate portion is provided between the two end portions and is configured to correspond to a region between a nasal bridge and a nasal tip of the user during use; and wherein the at least one attachment surface is provided on at least one surface of at least one of the two end portions and is configured to connect with at least one connecting member; and at least one connecting member comprising a first portion and a second portion, wherein the first portion is configured to be at least partially attached to at least one lateral region of the user’s nose, and wherein the second portion is configured to be connectable to the at least one attachment surface so as to detachably connect the support member to the at least one connecting member; wherein the second portion of the connecting member is configured to be connectable to the at least one attachment surface via hook-and-loop fastening, clasps, magnetic attraction, or chemical adhesive bonding.

2. The nasal dilation respiratory device according to claim 1, wherein the support member at least partially comprises semi-rigid materials or rigid materials.

3. The nasal dilation respiratory device according to claim 1, wherein the at least one attachment surface comprises at least one structure selected from the group consisting of a hook surface structure, a loop surface structure, and a composite surface structure.

4. The nasal dilation respiratory device according to claim 1, wherein the intermediate portion comprises at least one structure selected from the group consisting of an arched structure, a curved structure, and a linear structure.

5. The nasal dilation respiratory device according to claim 1, wherein the first portion of the connecting member comprises a medical adhesive material.

6. A nasal dilation respiratory device configured to be attached to a user’s nose to dilate a nasal cavity, comprising:

a support member configured to be provided adjacent to a nasal region of the user, the support member comprising two end portions, an intermediate portion, and at least one attachment surface;

wherein the two end portions are respectively formed at opposite ends of the support member;

wherein the intermediate portion is provided between the two end portions and is configured to correspond to a region between a nasal bridge and a nasal tip of the user during use; and wherein the at least one attachment surface is provided on a surface of at least one of the two end portions and is configured to connect with at least one connecting member; and at least one connecting member comprising a first portion and a second portion, wherein the first portion is configured to be at least partially attached to at least one lateral region of the user’s nose, and wherein the second portion of the connecting member is configured to be detachably adhered to the at least one attachment surface of the support member via hook-and-loop fastening.

7. The nasal dilation respiratory device according to claim 6, wherein a connection between the at least one attachment surface and the support member is formed by a method selected from the group consisting of integrally molding, ultrasonic welding, adhesive bonding, thermal pressing, and stitching.

8. The nasal dilation respiratory device according to claim 6, wherein the support member has a symmetrical structure.

9. The nasal dilation respiratory device according to claim 6, wherein the two end portions of the support member are curved along outer sides of the user’s nasal alae to conform to a nasal contour and enhance fixation.

10. The nasal dilation respiratory device according to claim 6, wherein an outer surface of the first portion of the at least one connecting member is coated with a skin-friendly layer to reduce skin irritation during prolonged wear.

11. The nasal dilation respiratory device according to claim 6, wherein the hook-and-loop fastening comprises a hook surface and a loop surface, the hook surface and the loop surface are configured to cooperate for repeatable attachment.

12. A nasal dilation respiratory device configured to be attached to a user’s nose to dilate a nasal cavity, comprising:

a support member configured to be provided adjacent to a nasal region of the user, the support member comprising two end portions, an intermediate portion, and at least one attachment surface;

wherein the two end portions are respectively formed at opposite ends of the support member;

wherein the intermediate portion is provided between the two end portions and is configured to correspond to a region between a nasal bridge and a nasal tip of the user during use; and wherein the at least one attachment surface is at least partially attached to at least one of the two end portions by mechanical connection, chemical bonding, and/or integrally molding; and at least one connecting member comprising a first portion and a second portion, wherein the first portion is configured to be at least partially attached to at least one lateral region of the user’s nose, and wherein the second portion is configured to be connected to the at least one attachment surface so as to detachably connect the support member to the at least one connecting member via hook-and-loop fastening, clasps, magnetic attraction, or chemical adhesive bonding;

wherein the respiratory device comprises at least one of the following characteristics:

the support member has a thickness of at least a portion thereof within a range of 0.1 mm to 20 mm;

the support member has a length within a range of 9 mm to 150 mm;

the support member has an angle within a range of 30 degrees to 180 degrees; and an area of the at least one connecting member attached to the user’s nose is within a range of 0.05 $cm^2$ to 20 $cm^2$.

13. The nasal dilation respiratory device according to claim 12, wherein the at least one connecting member is configured to be connected to the support member by a method selected from the group consisting of adhesive bonding, hook-and-loop fastening, mechanical engagement, magnetic attraction, and clasp connection, or any combination thereof.

14. The nasal dilation respiratory device according to claim 12, wherein the support member comprises a material having shape memory properties.

15. The nasal dilation respiratory device according to claim 12, wherein an area of the at least one attachment surface is less than or equal to an area of the second portion.

16. The nasal dilation respiratory device according to claim 12, wherein the first portion of the connecting member has a shape selected from the group consisting of circular, irregular, and polygonal shapes, the shape being configured to adapt to different nasal contours and enhance attachment stability.

17. The nasal dilation respiratory device according to claim 16, wherein different shapes of the first portion correspond to different contact areas, thereby providing directional support and adjustable adhesion force for different regions of the user's nasal alae.

18. A nasal dilation respiratory system configured to assist a user in dilating a nasal cavity, comprising:

a support member configured to be provided adjacent to a nasal region of the user, the support member comprising:

two end portions respectively formed at opposite ends of the support member and configured to correspond to outer regions of the user's nasal alae during use; and an intermediate portion provided between the two end portions and configured to correspond to a region between a nasal bridge and a nasal tip of the user during use;

at least one attachment surface on a surface of at least one of the two end portions and configured to connect with at least one connecting member; and the at least one connecting member, comprising:

a first portion configured to be at least partially attached to at least one lateral region of the user's nose; and a second portion of the connecting member configured to be detachably adhered to the at least one attachment surface via hook-and-loop fastening;

wherein a connection force generated between the support member and the at least one connecting member ranges from 2 gf to 200 gf; and wherein a nasal cavity dilation amplitude generated during use ranges from 0.1 mm to 20 mm.

19. The nasal dilation respiratory system according to claim 18, wherein the hook-and-loop fastening comprises a hook surface and a loop surface, and an adhesive strength between the hook surface and the loop surface is adjustable by varying a fastening area between the hook surface and the loop surface.

20. The nasal dilation respiratory system according to claim 18, wherein a thickness of the support member at least partially ranges from 0.1 mm to 20 mm.

21. The nasal dilation respiratory system according to claim 18, wherein the at least one attachment comprises a material selected from the group consisting of polyester, polyamide, polyurethane, polyolefin, and composites thereof.

22. The nasal dilation respiratory system according to claim 18, wherein a metal sheet is embedded within the support member, the metal sheet comprising a material selected from the group consisting of stainless steel, aluminum alloy, and shape memory alloy.

23. The nasal dilation respiratory system according to claim 18, wherein the intermediate portion is provided with a serrated structure, the serrated structure arranged along a longitudinal direction of the support member to form a plurality of bend angles, thereby providing a compliant structure.

24. The nasal dilation respiratory system according to claim 18, wherein a contact area between the first portion of the at least one connecting member and the user's nose ranges from 0.05 $cm^2$ to 20 $cm^2$.

* * * * *